United States Patent
Levin et al.

(10) Patent No.: US 6,200,996 B1
(45) Date of Patent: Mar. 13, 2001

(54) HETEROARYL ACETYLENIC SULFONAMIDE AND PHOSPHINIC ACID AMIDE HYDROXAMIC ACID TACE INHIBITORS

(75) Inventors: Jeremy I. Levin, New City, NY (US); James M. Chen, Bedminster; Frances C. Nelson, Wyckoff, both of NJ (US)

(73) Assignee: American Cyanamid Company, Madison, NJ (US)

( * ) Notice: Subject to any disclaimer, the term of this patent is extended or adjusted under 35 U.S.C. 154(b) by 0 days.

(21) Appl. No.: 09/492,976

(22) Filed: Jan. 27, 2000

Related U.S. Application Data
(60) Provisional application No. 60/155,229, filed on Jan. 27, 1999, now abandoned.

(51) Int. Cl.[7] .................... A61K 31/44; C07D 213/72; C07D 211/72; C07D 213/70; C07D 211/84
(52) U.S. Cl. .................... 514/347; 514/348; 514/349; 546/293; 546/294; 546/296; 546/297
(58) Field of Search .................. 546/296, 293, 546/294, 297; 514/347, 348, 349

(56) References Cited

U.S. PATENT DOCUMENTS

| | | |
|---|---|---|
| 5,455,258 | 10/1995 | MacPherson et al. . |
| 5,506,242 | 4/1996 | MacPherson et al. . |
| 5,552,419 | 9/1996 | MacPherson et al. . |
| 5,753,653 | 5/1998 | Bender et al. . |
| 5,770,624 | 6/1998 | Parker . |
| 5,804,593 | 9/1998 | Warpechoski et al. . |
| 5,817,822 | 10/1998 | Nantermet et al. . |
| 5,929,097 | 7/1999 | Levin et al. . |

FOREIGN PATENT DOCUMENTS

| | | |
|---|---|---|
| 195 42 189 | 5/1997 | (DE) . |
| 606046 | 12/1993 | (EP) . |
| 757037 | 7/1996 | (EP) . |
| 757984 | 8/1996 | (EP) . |
| 803505 | 4/1997 | (EP) . |
| WO9535275 | 12/1995 | (WO) . |
| WO9535276 | 12/1995 | (WO) . |
| WO9600214 | 1/1996 | (WO) . |
| WO9627583 | 9/1996 | (WO) . |
| WO9633172 | 10/1996 | (WO) . |
| WO9718194 | 5/1997 | (WO) . |
| WO9719068 | 5/1997 | (WO) . |
| WO9720824 | 6/1997 | (WO) . |
| WO9722587 | 6/1997 | (WO) . |
| WO9727174 | 7/1997 | (WO) . |
| WO9745402 | 12/1997 | (WO) . |
| WO9803166 | 1/1998 | (WO) . |
| WO9807697 | 2/1998 | (WO) . |
| WO9808815 | 3/1998 | (WO) . |
| WO9808822 | 3/1998 | (WO) . |
| WO9808823 | 3/1998 | (WO) . |
| WO9808825 | 3/1998 | (WO) . |
| WO9808827 | 3/1998 | (WO) . |
| WO9808853 | 3/1998 | (WO) . |
| WO9816503 | 4/1998 | (WO) . |
| WO9816506 | 4/1998 | (WO) . |
| WO9816514 | 4/1998 | (WO) . |
| WO9816520 | 4/1998 | (WO) . |
| WO9827069 | 6/1998 | (WO) . |
| WO9831664 | 7/1998 | (WO) . |
| WO9833768 | 8/1998 | (WO) . |
| WO9834918 | 8/1998 | (WO) . |
| WO9839313 | 9/1998 | (WO) . |
| WO9839329 | 9/1998 | (WO) . |
| WO9842659 | 10/1998 | (WO) . |
| WO9843963 | 10/1998 | (WO) . |

OTHER PUBLICATIONS

Allabergenov et. al., "Corrosion Inhibiting Effect of Acetylenic Amino Ethers Of Substituted Phenols", Izv. Vyssh. Uchebn., Khim. Tekhnol., pp. 478–480, vol. 21 (4), 1978.*
Shire, M.G., Exp. Opin. Ther. Patents 8(5), 531 (1998).
Grossman, J.M., Women's Health, 6(6), 627 (1997).
Isomaki, P.J., Ann. Med., 29, 499 (1997).
Camussi, G., Drugs, 55(5), 613 (1998).
Mathison et al., J. Clin. Invest., 81, 1925, (1988).
Miethke et al., J. Exp. Med., 175, 91 (1992).
Piquet, P. F., J. Exp. Med. 166, 1280 (1987).
Beuther, B., Ann. Rev., Biochem, 57, 505 (1988).
Ksontini, R., Arch, Surg., 133, 558, (1998).
Packer, M., Circulation, 92(6), 1379 (1995).
Ferrari, R., et al., Circulation 92(6), 1479 (1995).
Hotamisligil, G.S. et al., Science, 259, 87 (1993).
Peterson, P.K. et al., J. Clin. Invest., 89, 574 (1992).
Pallares–Trujillo et al., Med. Res. Reviews, 15(6), 533 (1995).
Old, L., Science, 230, 630 (1985).
Rankin, E.C. et al., Br. J. Rheumatol., 34, 334 (1995).
Pharmaprojects, Therapeutic Updates 17 (Oct.) au 197, M2Z (1996).
McGeehan et al, Current Pharmaceutical Design, 2, 662 (1996).
Script 20, 2349 (1998).
MacPherson et al., J. Med. Chem., 40, 2525 (1997).
Tamura et al., J. Med. Chem. 41, 640 (1998).
Levin et al., Bioorg & Med. Chem. Letters, 8, 2657 (1998).
Pikul et al., J. Med. Chem., 41, 3568 (1998).

* cited by examiner

*Primary Examiner*—John Kight
*Assistant Examiner*—Binta Robinson
(74) *Attorney, Agent, or Firm*—Rebecca R. Barrett

(57) ABSTRACT

Compounds of the formula:

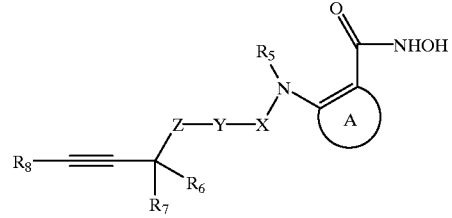

are useful in treating disease conditions mediated by TNF-α such as rheumatoid arthritis, osteoarthritis, sepsis, AIDS, ulcerative colitis, multiple sclerosis, Crohn's disease and degenerative cartilage loss.

12 Claims, No Drawings

HETEROARYL ACETYLENIC SULFONAMIDE AND PHOSPHINIC ACID AMIDE HYDROXAMIC ACID TACE INHIBITORS

This application claims the benefit of U.S. Provisional Application No. 60/155,229, filed Jan. 27, 1999.

FIELD OF INVENTION

This invention relates to acetylenic aryl and heteroaryl sulfonamide and phosphinic acid amide hydroxamic acids which act as inhibitors of TNF-α converting enzyme (TACE). The compounds of the present invention are useful in disease conditions mediated by TNF-α such as rheumatoid arthritis, osteoarthritis, sepsis, AIDS, ulcerative colitis, multiple sclerosis, Crohn's disease and degenerative cartilage loss.

BACKGROUND OF THE INVENTION

TNF-α converting enzyme (TACE) catalyzes the formation of TNF-α from membrane bound TNF-α precursor protein. TNF-α is a pro-inflammatory cytokine that is believed to have a role in rheumatoid arthritis [Shire, M. G.; Muller, G. W. *Exp. Opin. Ther. Patents* 1998, 8(5), 531; Grossman, J. M.; Brahn, E. *J. Women's Health* 1997, 6(6), 627; Isomaki, P.; Punnonen, *J. Ann. Med.* 1997, 29, 499; Camussi, G.; Lupia, E. *Drugs*, 1998, 55(5), 613.] septic shock [Mathison, et. al. *J. Clin. Invest.* 1988, 81, 1925; Miethke, et. al. *J. Exp. Med.* 1992, 175, 91.], graft rejection [Piguet, P. F.; Grau, G. E.; et. al. *J. Exp. Med.* 1987, 166, 1280.], cachexia [Beutler, B.; Cerami, A. *Ann. Rev. Biochem.* 1988, 57, 505.], anorexia, inflammation [Ksontini, R,; MacKay, S. L. D.; Moldawer, L. L. *Arch. Surg.* 1998, 133, 558.], congestive heart failure [Packer, M. *Circulation,* 1995, 92(6), 1379; Ferrari, R.; Bachetti, T.; et. al. *Circulation,* 1995, 92(6), 1479.], post-ischaemic reperfusion injury, inflammatory disease of the central nervous system, inflammatory bowel disease, insulin resistance [Hotamisligil, G. S.; Shargill, N. S.; Spiegelman, B. M.; et al. *Science,* 1993, 259, 87.] and HIV infection [Peterson, P. K.; Gekker, G.; et. al. *J. Clin. Invest.* 1992, 89, 574; Pallares-Trujillo, J.; Lopez-Soriano, F. J. Argiles, J. M. *Med. Res. Reviews,* 1995, 15(6), 533.]], in addition to its well-documented antitumor properties [Old, L. *Science,* 1985, 230, 630.]. For example, research with anti-TNF-α antibodies and transgenic animals has demonstrated that blocking the formation of TNF-α inhibits the progression of arthritis [Rankin, E. C.; Choy, E. H.; Kassimos, D.; Kingsley, G. H.; Sopwith, A. M.; Isenberg, D. A.; Panayi, G. S. Br. *J. Rheumatol.* 1995, 34, 334; *Pharmaprojects,* 1996, Therapeutic Updates 17 (Oct.), au197-M2Z.]. This observation has recently been extended to humans as well as described in "TNF-α in Human Diseases", *Current Pharmaceutical Design,* 1996, 2, 662.

It is expected that small molecule inhibitors of TACE would have the potential for treating a variety of disease states. Although a variety of TACE inhibitors are known, many of these molecules are peptidic and peptide-like which suffer from bioavailability and pharmacokinetic problems. In addition, many of these molecules are non-selective, being potent inhibitors of matrix metalloproteinases and, in particular, MMP-1. Inhibition of MMP-1 (collagenase 1) has been postulated to cause joint pain in clinical trials of MMP inhibitors [Scrip, 1998, 2349, 20]. Long acting, selective, orally bioavailable non-peptide inhibitors of TACE would thus be highly desirable for the treatment of the disease states discussed above.

Examples of sulfonamide hydroxamic acid MMP/TACE inhibitors in which a 2 carbon chain separates the hydroxamic acid and the sulfonamide nitrogen, as shown below, are disclosed in WIPO international publications WO9816503, WO9816506, WO9816514 and WO9816520 and U.S. Pat. No. 5,776,961.

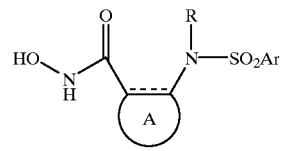

U.S. Pat. Nos. 5,455,258, 5,506,242, 5,552,419, 5,770,624, 5,804,593 and 5,817,822 as well as European patent application EP606,046A1 and WIPO international publications WO9600214 and WO9722587 disclose non-peptide inhibitors of matrix metalloproteinases and/or TACE of which the aryl sulfonamide hydroxamic acid shown below, in which 1 carbon separates the hydroxamic acid and the sulfonamide nitrogen, is representative. Additional publications disclosing sulfonamide based MMP inhibitors which are variants of the sulfonamide-hydroxamate shown below, or the analogous sulfonamide-carboxylates, are European patent applications EP-757037-A1 and EP-757984-A1 and WIPO international publications WO9535275, WO9535276, WO9627583, WO9719068, WO9727174, WO9745402, WO9807697, and WO9831664, WO9833768, WO9839313, WO9839329, WO9842659 and WO9843963. The discovery of this type of MMP inhibitor is further detailed by MacPherson, et. al. in *J. Med. Chem.,* (1997), 40, 2525 and Tamura, et. al. in *J. Med. Chem.* (1998), 41, 640.

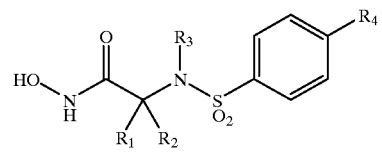

Publications disclosing β-sulfonamide-hydroxamate inhibitors of MMPs and/or TACE in which the carbon alpha to the hydroxamic acid has been joined in a ring to the sulfonamide nitrogen, as shown below, include U.S. Pat. No. 5,753,653, WIPO international publications WO9633172, WO9720824, WO9827069, WO9808815, WO9808822, WO9808823, WO9808825, WO9834918, WO9808827, Levin, et. al. *Bioorg. & Med. Chem. Letters* 1998, 8, 2657 and Pikul, et. al. *J. Med. Chem.* 1998, 41, 3568.

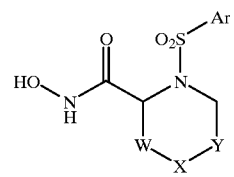

The patent applications DE19,542,189-A1, WO9718194, and EP803505 disclose additional examples of cylic sulfonamides as MMP and/or TACE inhibitors. In this case the sulfonamide-containing ring is fused to a aromatic or heteroaromatic ring.

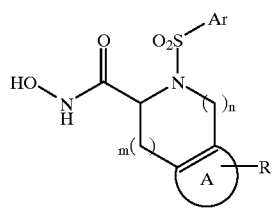

Analogous to the sulfonamides are the phosphinic acid amide hydroxamic acid MMP/TACE inhibitors, exemplified by the structure below, which have been disclosed in WIPO international publication WO9808853.

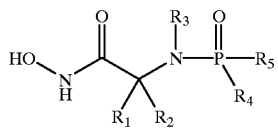

Sulfonamide MMP/TACE inhibitors in which a thiol is the zinc chelating group, as shown below, have been disclosed in WIPO international application 9803166.

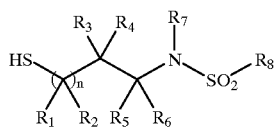

It is an object of this invention to disclose aryl and heteroaryl sulfonamide and phosphinic acid amide hydroxamic acid MMP/TACE inhibitors in which the sulfonyl aryl group is para-substituted with a substituted butynyl moiety or a propargylic ether, amine or sulfide. These compounds provide enhanced levels of inhibition of the activity of TACE in vitro and in a cellular assay and/or selectivty over MMP-1. These compounds may therefore be used in the treatment of diseases mediated by TNF.

SUMMARY OF THE INVENTION

The TACE and MMP inhibiting ortho-sulfonamido and phosphinic acid amide aryl and heteroaryl hydroxamic acids of the present invention are represented by the formula:

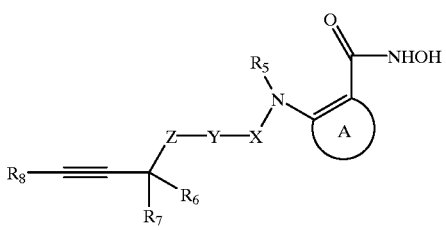

where the C(=O)NHOH moiety and the —$NR^5$— moiety are bonded to adjacent carbons of group A; wherein A is 5–6 membered heteroaryl having 1 to 3 heteroatoms selected from N, NR9, S and O;
X is $SO_2$ or —$P(O)R_{10}$;
Y is aryl or 5–10 membered mono- or bi-cyclic heteroaryl having from 1 to three heteroatoms selected from N, NR9, S and O, with the proviso that X and Z may not be bonded to adjacent atoms of Y;
Z is O, NH, $CH_2$ or S;
$R_5$ is hydrogen or alkyl of 1–6 carbon atoms;
$R_6$ and $R_7$ are each, independently, hydrogen, alkyl of 1–6 carbon atoms, —CN, —CCH;
$R_8$ is hydrogen, alkyl of 1–6 carbon atoms, alkenyl of 2–6 carbon atoms, alkynyl of 2–6 carbon atoms, cycloalkyl of 3–6 carbon atoms, aryl, 5 to 10 membered heteroaryl having 1 to 3 heteroatoms selected from N, NR9, S and O, or 5 to 9 membered heterocycloalkyl having 1 or 2 heteroatoms selected from N, NR9, S and O;
$R_9$ is hydrogen, aryl, alkyl of 1–6 carbon atoms or cycloalkyl of 3–6 carbon atoms; and $R_{10}$ is alkyl of 1–6 carbon atoms, cycloalkyl of 3–6 carbon atoms, aryl, or heteroaryl; or a pharmaceutically acceptable salt thereof.

Preferred compounds of this invention are those of structure B wherein both carbons of A adjacent the —$NR^5$— group have a substituent other than hydrogen.

More preferred compounds of this invention include compounds of structure B in which A is a 5–6 membered heteroaryl having 1 to 3 heteroatoms selected from N, NR9, S and O wherein:
both carbons of A adjacent the —$NR^5$— group have a substituent other than hydrogen;
and Y is a phenyl ring substituted at the 1- and 4-positions by X and Z, respectively.

More preferred compounds of this invention include compounds of structure B in which A is a phenyl wherein:
both carbons of A adjacent the —$NR^5$— group have a substituent other than hydrogen;
Y is a phenyl ring substituted at the 1- and 4-positions by X and Z, respectively;
and X is $SO_2$.

More preferred compounds of this invention include compounds of structure B in which A is a phenyl wherein:
both carbons of A adjacent the —$NR^5$— group have a substituent other than hydrogen;
Y is a phenyl ring substituted at the 1- and 4-positions by X and Z, respectively;
X is $SO_2$;
Z is oxygen;
and $R_6$ and $R_7$ are hydrogen.

More preferred compounds of this invention include compounds of structure B in which A is a phenyl wherein:
both carbons of A adjacent the —$NR^5$— group have a substituent other than hydrogen;
Y is a phenyl ring substituted at the 1- and 4-positions by X and Z, respectively;
X is $SO_2$;
Z is oxygen;
$R_6$ and $R_7$ are hydrogen;
and $R_8$ is —$CH_2OH$ or methyl.

Heteroaryl, as used throughout, is a 5–10 membered mono- or bicyclic ring having from 1–3 heteroatoms selected from N, NR9, S and O. Heteroaryl is preferably

-continued

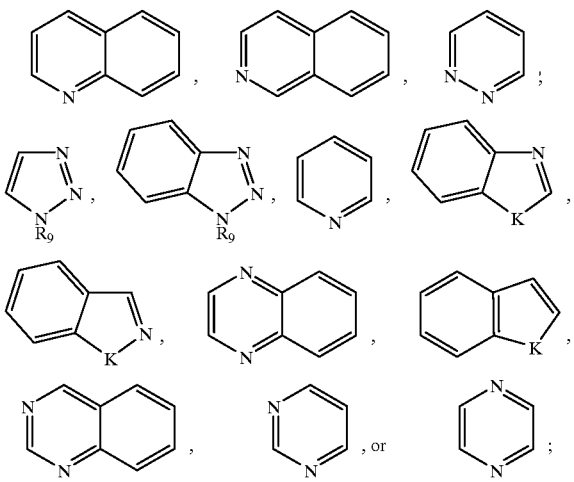

wherein K is NR9, O or S and R9 is hydrogen, phenyl, naphthyl, alkyl of 1–6 carbon atoms, or cycloalkyl of 3–6 carbon atoms. Preferred heteroaryl rings include pyrrole, furan, thiophene, pyridine, pyrimidine, pyridazine, pyrazine, triazole, pyrazole, imidazole, isothiazole, thiazole, isoxazole, oxazole, indole, isoindole, benzofuran, benzothiophene, quinoline, isoquinoline, quinoxaline, quinazoline, benzotriazole, indazole, benzimidazole, benzothiazole, benzisoxazole, and benzoxazole.

For purposes of the definition of A, It is still more preferred that A is a heteroaryl selected from

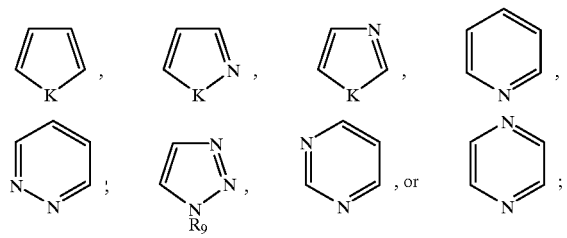

Heteroaryl groups of the present invention may optionally be mono- or di-substituted.

Heterocycloalkyl as used herein refers to a 5 to 10 membered saturated or unsaturated mono or bi-cyclic ring having 1 or 2 heteroatoms selected from N, NR9, S or O. Heterocycloalkyl rings of the present invention are preferably selected from

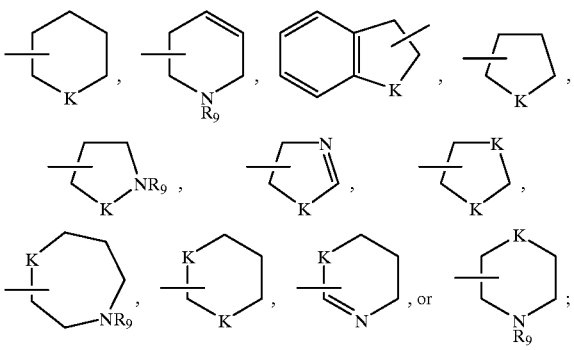

wherein K is NR9, O or S and R9 is hydrogen, phenyl, naphthyl, alkyl of 1–6 carbon atoms, or cycloalkyl of 3–6 carbon atoms. Preferred heterocycloalkyl rings include piperidine, piperazine, morpholine, tetrahydropyran, tetrahydrofuran or pyrrolidine. Heterocycloalkyl groups of the present invention may optionally be mono- or di-substituted.

Aryl, as used herein refers phenyl or naphthyl which may, optionally be mono-, di- or tri-substituted.

Alkyl, alkenyl, alkynyl, and perfluoroalkyl include both straight chain as well as branched moieties. Alkyl, alkenyl, alkynyl, and cycloalkyl groups may be unsubstituted unsubstituted (carbons bonded to hydrogen, or other carbons in the chain or ring) or may be mono- or poly-substituted.

Halogen means bromine, chlorine, fluorine, and iodine.

Suitable substituents of aryl, heteroaryl, alkyl, alkenyl, alkynyl, cycloalkyl and include, but are not limited to halogen, alkyl of 1–6 carbon atoms, alkenyl of 2–6 carbon atoms, alkynyl of 2–6 carbon atoms, cyclocalkyl of 3–6 carbon atoms, —$OR_2$, —CN, —$COR_2$, perfluoroalkyl of 1–4 carbon atoms, —O-perfluoroalkyl of 1–4 carbon atoms, —$CONR_2R_3$, —$S(O)_nR_2$—$OPO(OR_2)OR_3$, —$PO(OR_2)R_3$, —$OC(O)NR_2R_3$, —$C(O)NR_2OR_3$, —$COOR_2$, —$SO_3H$, —$NR_2R_3$, —$N[(CH_2)_2]_2NR_2$, —$NR_2COR_3$, —$NR_2COOR_3$, —$SO_2NR_2R_3$, —$NO_2$, —$N(R_2)SO_2R_3$, —$NR_2CONR_2R_3$, —$NR_2C(=NR_3)NR_2R_3$, —$NR_2C(=NR)N(SO_2R_2)R_3$, $NR_2C(=NR_3)N(C=OR_2)R_3$, —$SO_2NHCOR_4$, —$CONHSO_2R_4$, -tetrazol-5-yl, —$SO_2NHCN$, —$SO_2NHCONR_2R_3$, phenyl, naphthyl, heteroaryl or heterocycloalkyl;

wherein —$NR_2R_3$ may form a pyrrolidine, piperidine, morpholine, thiomorpholine, oxazolidine, thiazolidine, pyrazolidine, piperazine, or azetidine ring;

$R_2$ and $R_3$ are each, independently, hydrogen, alkyl of 1–6 carbon atoms, cycloalkyl of 3–6 carbon atoms, phenyl, naphthyl, heteroaryl or heterocycloalkyl;

$R_4$ is alkyl of 1–6 carbon atoms, alkenyl of 2–6 carbon atoms, alkynyl of 2–6 carbon atoms, cycloalkyl of 3–6 carbon atoms; perfluoroalkyl of 1–4 carbon atoms, phenyl, naphthyl, heteroaryl or heterocycloalkyl; and n is 0 to 2.

Suitable substituents of heterocycloalkyl groups of the present invention include, but are not limited to alkyl of 1–6 carbon atoms, cycloalkyl of 3–6 carbon atoms, phenyl, naphthyl, heteroaryl and heterocycloalkyl.

When a moiety contains more than substituent with the same designation each of those substituents may be the same or different.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable acids when a compound of this invention contains a basic moiety. Salts may also be formed from organic and inorganic bases, preferably alkali metal salts, for example, sodium, lithium, or potassium, when a compound of this invention contains an acidic moiety.

The compounds of this invention may contain an asymmetric carbon atom and some of the compounds of this invention may contain one or more asymmetric centers and may thus give rise to optical isomers and diastereomers. While shown without respect to stereochemistry, the present invention includes such optical isomers and diastereomers; as well as the racemic and resolved, enantiomerically pure R and S stereoisomers; as well as other mixtures of the R and S stereoisomers and pharmaceutically acceptable salts thereof. It is recognized that one optical isomer, including diastereomer and enantiomer, or stereoisomer may have favorable properties over the other. Thus when disclosing and claiming the invention, when one racemic mixture is disclosed, it is clearly contemplated that both optical isomers, including diastereomers and enantiomers, or stereoisomers substantially free of the other are disclosed and claimed as well.

The compounds of this invention are shown to inhibit the enzymes MMP-1, MMP-9, MMP-13 and TNF-α converting enzyme (TACE) and are therefore useful in the treatment of arthritis, tumor metastasis, tissue ulceration, abnormal wound healing, periodontal disease, graft rejection, insulin resistance, bone disease and HIV infection. In particular, the compounds of the invention provide enhanced levels of inhibition of the activity of TACE in vitro and in cellular assay and/or enhanced selectivity over MMP-1 and are thus particularly useful in the treatment of diseases mediated by TNF.

The invention is further directed to a process for making compounds of structure B involving one or more reactions as follows:
1) alkylating a compound of formula I, or a salt or solvate thereof,

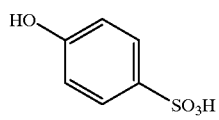

I into a compound of formula II

II

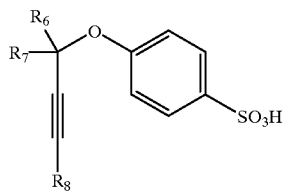

2) reacting a compound of formula II above, or a salt or solvate thereof, with a chlorinating agent such as thionyl chloride, chlorosulfonic acid, oxalyl chloride, phosphorus pentachloride, or other halogenating agents such as fluorosulfonic acid or thionyl bromide to a compound of formula III:

III

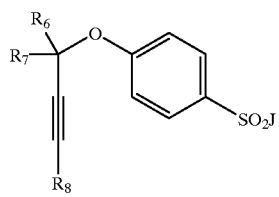

wherein J is fluorine, bromine, chlorine.

The resultant sulfonyl chloride, fluoride or bromide, may be further converted to triazolide, imidazolide or benzothiazolide derivatives, where J is 1,2,4-triazolyl, imzotriazolyl or imidazol-yl, by reacting the compound with 1,2,4-triazole, midazole or benzotriazole, respectively. $R_6$, $R_7$ and $R_8$ are as defined above.

The invention is still further directed to a process for making compounds of structure B involving one or more reactions as follows:

1) alkylating phenol, or a salt or solvate thereof, into a compound of formula IV:

IV

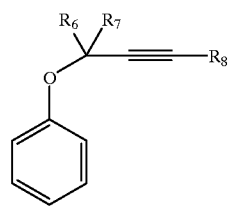

2) reacting a compound of formula IV above, or a salt or solvate thereof with chlorosulfonic acid to prepare a compound of formula II above.

Particularly preferred intermediates are compounds of formulae II and III, with the proviso that R6 is not hydrogen.

The invention compounds are prepared using conventional techniques known to those skilled in the art of organic synthesis. The starting materials used in preparing the compounds of the invention are known, made by known methods or are commercially available. The following compounds (V–IX) which may be used in preparing compounds of the invention are known and references are given herein below. This list is included for illustrative purposes only and is not to be construed as limiting in any way.

V

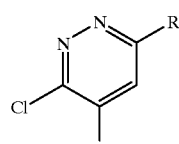

VI

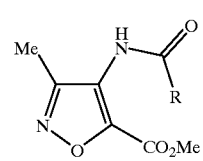

VII

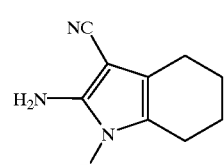

VIII

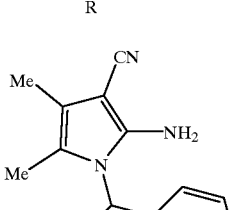

IX

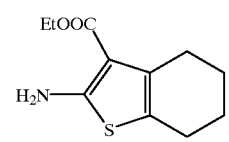

Literature references for these materials are as follows:
Compound V:

a) Dolle, R E; Hoyer, D W; Schmidt, S J; Ross, T M; Rinker, J M; Ator, M A Eur. Pat. Appl. EP-628550.

b) Wermuth, C-G; Schlewer, G; Bourguignon, J-J; Maghioros, G; Bouchet, M-J et. al. J. Med. Chem (1989), 32, 528–537.

c) Yutugi, S et. al. Chem. Pharm. Bull, (1971) 19, 2354–2364.

d) Dolle, R E; Hoyer, D; Rinker, J M; Ross, T M; Schmidt, S J Biorg. Med. Chem. Lett (1977) 7, 1003–1006.

Compound VI:

Camparini, A; Ponticelli, F; Tedeschi, P. J. Chem. Soc., Perkin Trans.1 (1982), 10,2391-4.

Compound VII:

Muller, C. E.; Geis, U.; Grahner, B.; Lanzner, W.; Eger, K. J. Med. Chem. (1996), 39, 2482.

Compound VIII:

Muller, C. E.; Geis, U.; Grahner, B.; Lanzner, W.; Eger, K. J. Med. Chem. (1996), 39, 2482.

Compound IX:
Commercially available.

Those skilled in the art will recognize that certain reactions are best carried out when other potentially reactive functionality on the molecule is masked or protected, thus avoiding undesirable side reactions and/or increasing the yield of the reaction. To this end, those skilled in the art may use protecting groups. Examples of these protecting group moieties may be found in T. W. Greene, P. G. M. Wuts "*Protective Groups in Organic Synthesis*", 2$^{nd}$ Edition, 1991, Wiley & Sons, New York. Reactive side chain functionalities on amino acid starting materials are preferably protected. The need and choice of protecting groups for a particular reaction is known to those skilled in the art and depends on the nature of the functional group to be protected (hydroxy, amino, carboxy, etc.), the structure and stability of the molecule of which the substituent is part and the reaction conditions.

When preparing or elaborating compounds of the invention containing aryl, heteroaryl or heterocyclic rings, those skilled in the art recognize that substituents on that ring may be prepared before, after or concomitant with construction of the ring. For clarity, substituents on such rings have been omitted from the schemes herein below.

Those skilled in the art will recognize that the nature and order of the synthetic steps presented may be varied for the purpose of optimizing the formation of the compounds of the invention.

The hydroxamic acid compounds of the invention, 1, are prepared according to Scheme 1 by converting a carboxylic acid, 2, into the corresponding acid chloride or anhydride, or by reacting it with a suitable peptide coupling reagent, followed by reaction with hydroxylamine to give 1, or with a protected hydroxylamine derivative to give 3. Compounds 3, wherein $R_{30}$ is a t-butyl, benzyl, trialkylsilyl or other suitable masking group may then be deprotected by known methods to provide the hydroxamic acid 1.

Scheme 1:

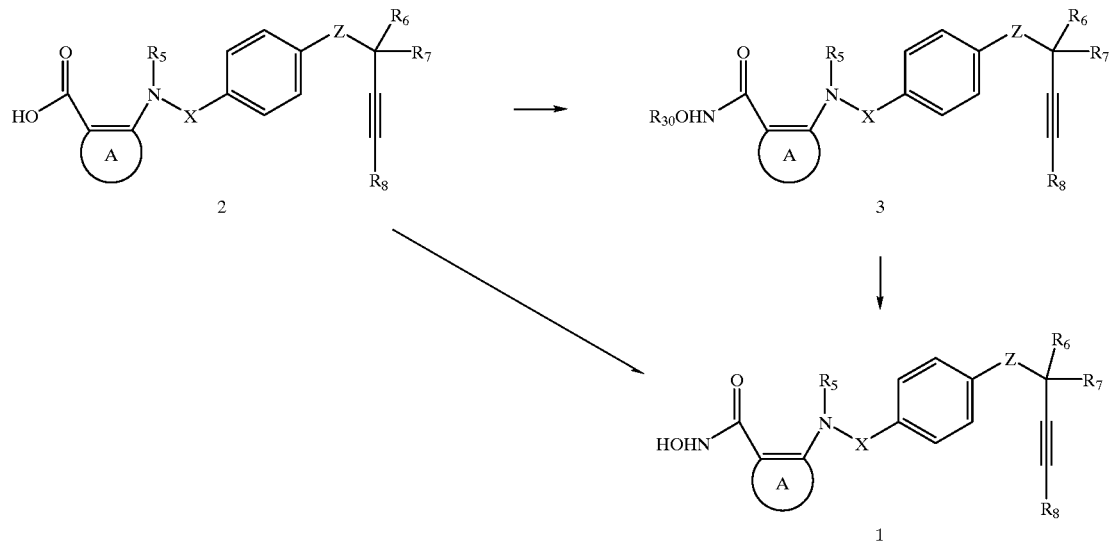

Carboxylic acids 2 may be prepared as shown in Scheme 2. Amino acid derivative 4, in which $R_{40}$ is hydrogen or a suitable carboxylic acid protecting group, may be sulfonylated or phosphorylated by reacting with compounds 5, in which J is a suitable leaving group including, but not limited to chlorine. The N—H compound 6 may then be alkylated with $R_3J$ and a base such as potassium carbonate or sodium hydride in a polar aprotic solvent such as acetone, N,N-dimethylformamide (DMF), or tetrahydrofuran (THF) to provide sulfonamide 7. Compound 7 is also available through direct reaction of 5 with an N-substituted amino acid derivative, 8. Conversion of 7 into the carboxylic acid is performed by acid, base hydrolysis, or other method consistent with the choice of protecting group $R_{40}$ and the presence of a carbon-carbon triple bond.

Scheme 2:

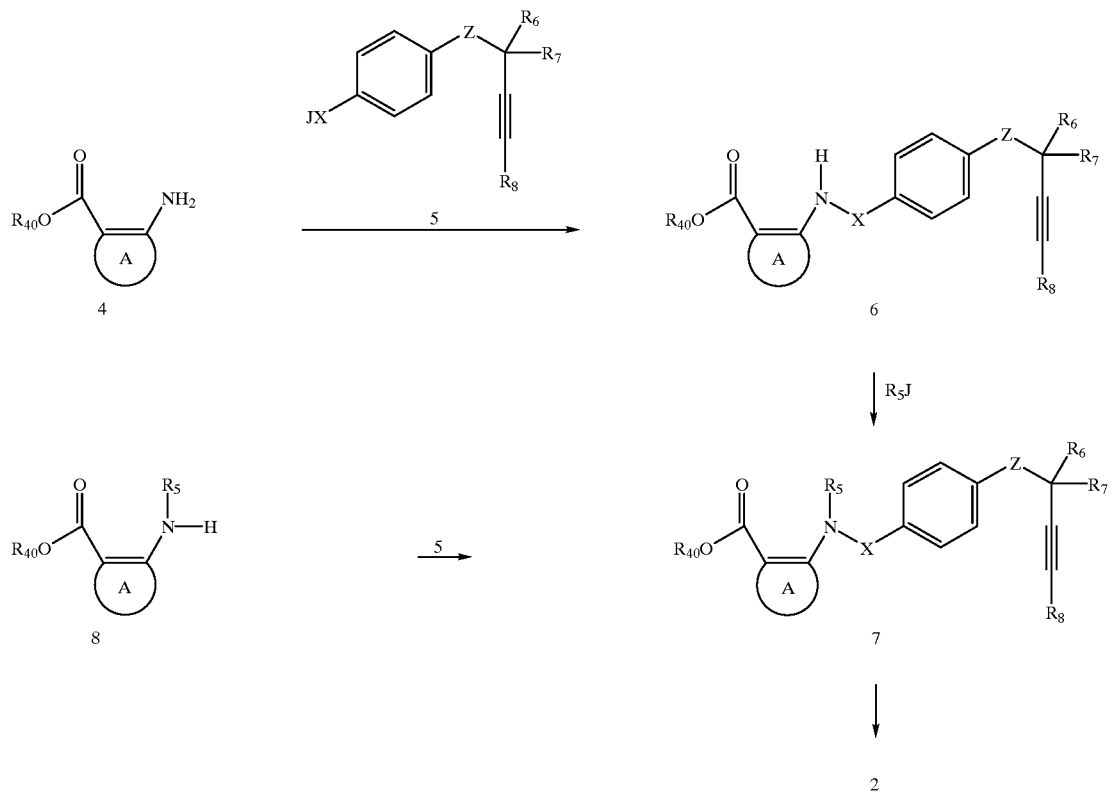

Methods of preparation of sulfonylating agents 5 are shown in Scheme 3. Thus, sulfonic acid salts 9, where $ZR_{50}$ is a hydroxy, thiol or substituted amino moiety may be alkylated with acetylenes 10, where J is a suitable leaving group such as halogen mesylate, tosylate, or triflate to give 11. Acetylenes 10 are commercially available or known compounds, or they may be synthesized by known methods by those skilled in the art. The sulfonic acid salts 11 may be converted into the corresponding sulfonyl chloride or other sulfonylating agent 5 by known methods, such as reaction with oxalyl chloride or other reagent compatible with substituents $R_6$, $R_7$ and $R_8$ and the acetylene. Alternatively, the disulfide 12 may be converted into di-acetylene 13 by reaction with compounds 10, followed by reduction of the disulfide bond to provide the analogous thiols which may be converted into 5 by known methods. Alkylation of the phenol, thiophenol, aniline or protected aniline 14 with 10 to give 15, followed by reaction with chlorosulfonic acid provide sulfonic acids 16 which are readily converted into 5 with oxalyl chloride or similar reagents. Thiophenols 17 are also precursors to 5 via protection of the thiol, alkylation of ZH, where Z is O, N or S, and deprotection of the sulfur followed by oxidation to the sulfonic acid 16.

Scheme 3:

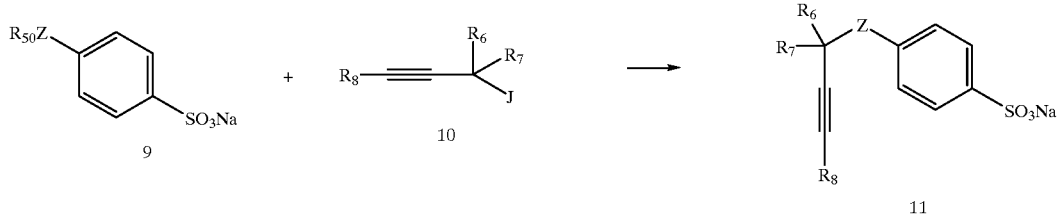

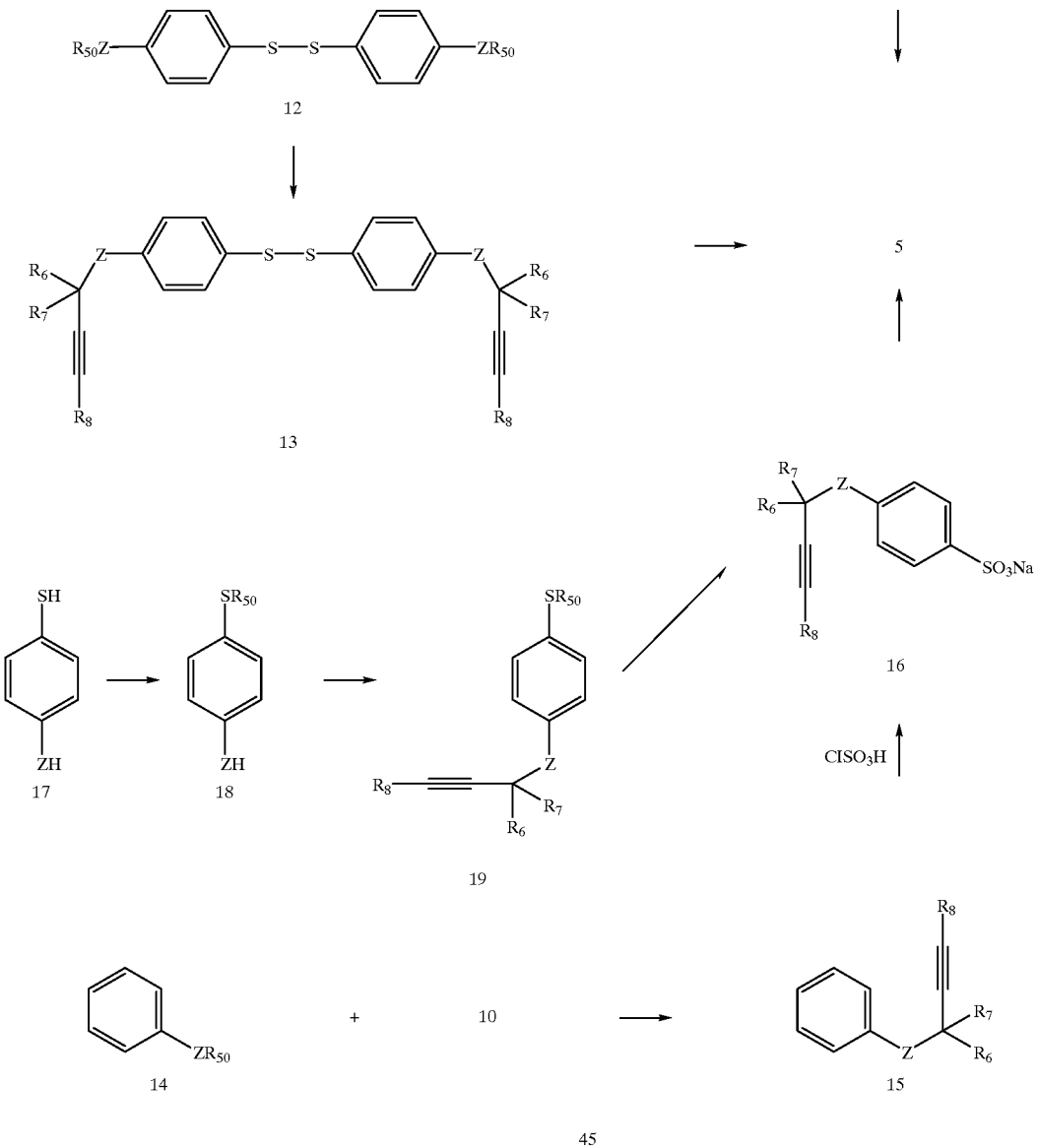
The phosphorus containing analogs of 8 may be prepared using similar methodology, as shown in Scheme 4.
Scheme 4:
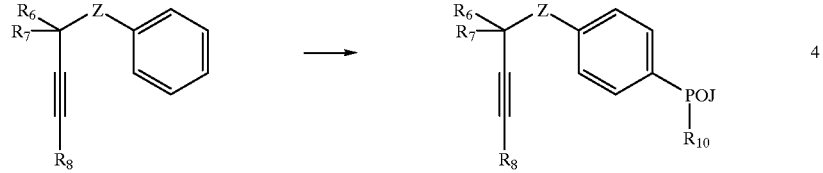

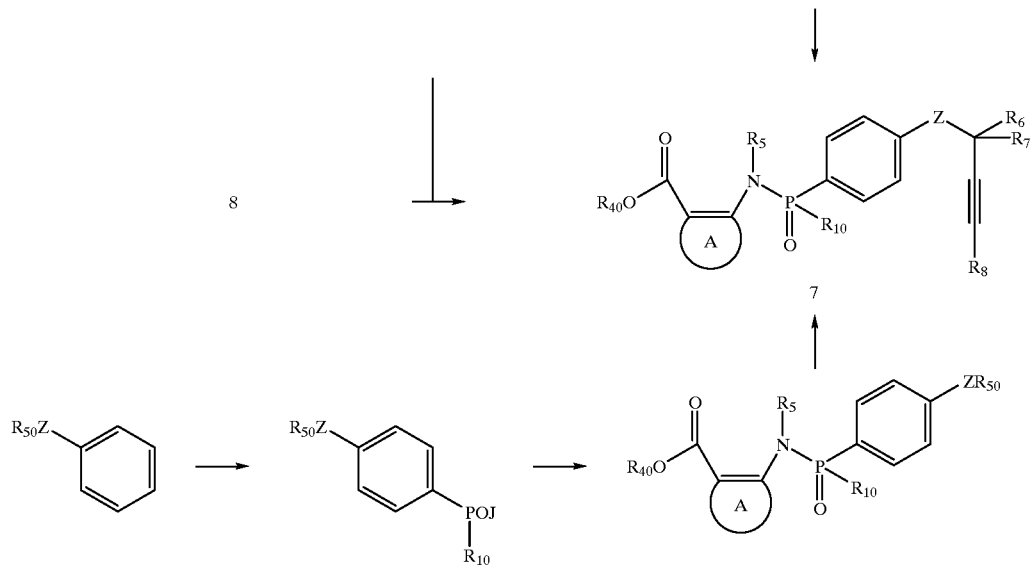

The acetylenic side chain may also be appended after sulfonylation or phosphorylation of the amino acid derivative, as shown in Scheme 5. Thus, the amino acid derivatives 4 and 8 can be sulfonylated or phosphorylated with compounds 20, where $ZR_{50}$ is hydroxy or protected hydroxy, thiol or amine, and, if necessary, alkylated with $R_7J$ as in Scheme 2, to give 21. Removal of the $R_{50}$ masking group to give 22 and subsequent alkylation of the resulting phenol, thiol or amine with 10 provides 7. In the case where $ZR_{50}$ is equal to OH, no deprotection step is required to give 22.

4 and/or 8. Sulfonylation or phosphorylation with para-nitro aryl compound 23, for example 4-nitrobenzenesulfonyl chloride, followed by alkylation with $R_5J$ (for 4) using a base such as potassium carbonate or sodium hydride in DMF provides 24. Reduction of the nitro moiety with hydrogen and palladium on carbon, tin chloride or other known method to give aniline 25 and subsequent alkylation with 10 then provides 7. Aniline 25 may be derivatized with a suitable nitrogen protecting group, such as t-butoxycarbonyl, to give 26 prior to alkylation with 10 subsequent deprotection after the alkylation step.

Scheme 5:

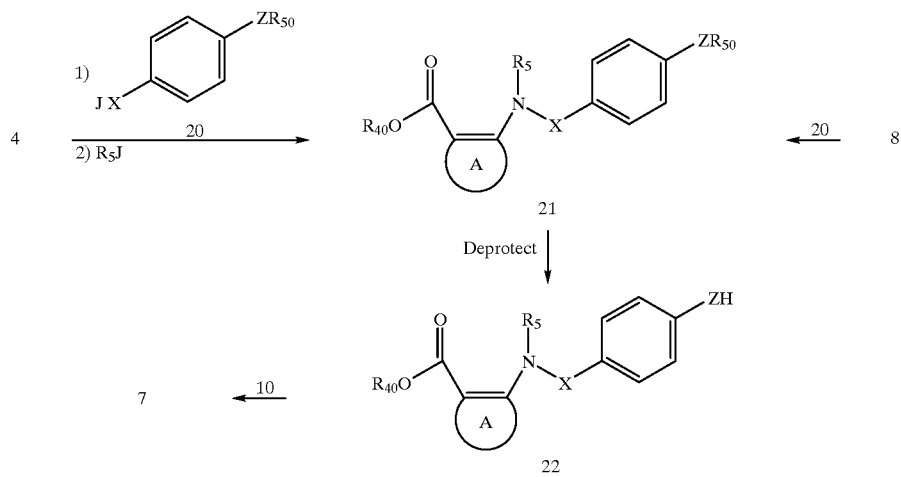

The propargylic amine analogs of 7 can be synthesized as shown in Scheme 6 starting from the amino acid derivatives Scheme 6:

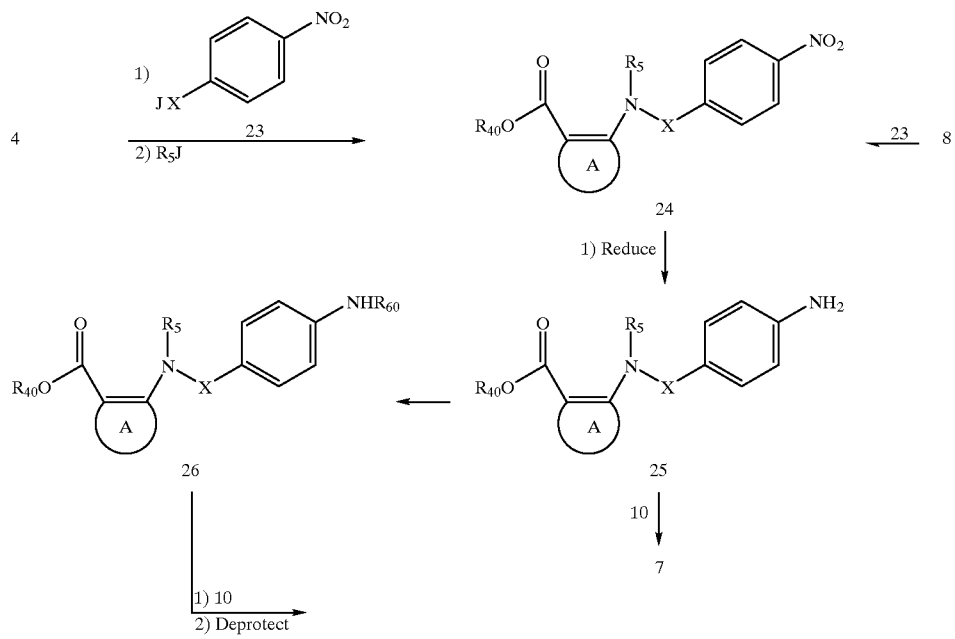

Acetylenic derivatives 7 are also accessible via the fluoro compounds 27, readily prepared from the amino acid derivatives 4 and/or 8 by reaction with fluoraryl 26, as shown in Scheme 7. Displacement of the fluorine of 27 in the presence of a base such as sodium hydride with a masked hydroxy, thiol, or amino group ($HZR_{70}$, where $R_{70}$ is a suitable protecting group) in a polar aprotic solvent such as DMF, followed by deprotection gives 28, which can then be alkylated with 10 to provide 7. Conversion of 27 to 28, where Z is sulfur, might also be accomplished with $Na_2S$, $K_2S$, NaSH or KS(C=S)OEt. The fluorine of 27 can also be displaced in a polar aprotic solvent with the propargylic derivative 29, where Z is O, S or NH, in the presence of a base such as sodium hydride, to give 7 directly.

Scheme 7:

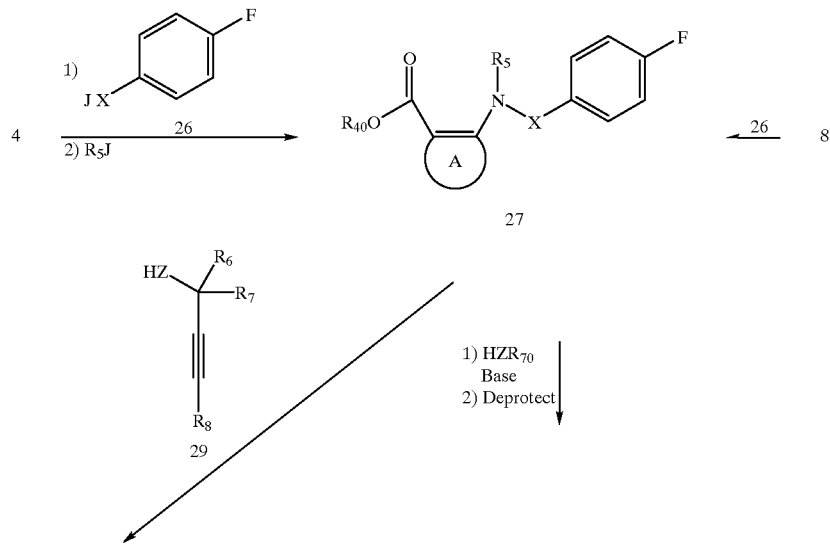

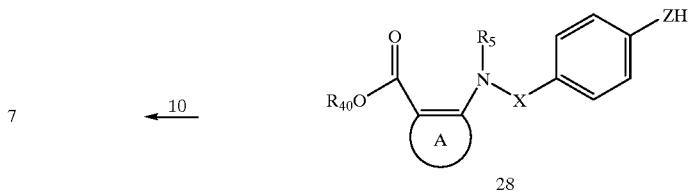

Compound 7, wherein Z is a methylene group, is available via 30, as shown in Scheme 8. Benzylic bromination of 30 with N-bromosuccinimide in a chlorinated hydrocarbon solvent provides bromide 31. This is followed by displacement of the bromide with the appropriate propynyl cuprate to provide sulfonamide 8.

bromide 36 which may be displaced with a variety of nucleophiles to give, for example, ethers, thioethers and amines 37. Palladium catalyzed coupling reactions of 32 provide the aryl or heteroaryl acetylenes 38. It is recognized by those skilled in the art of organic synthesis that the successful use of these methods is dependent upon the Scheme 8:

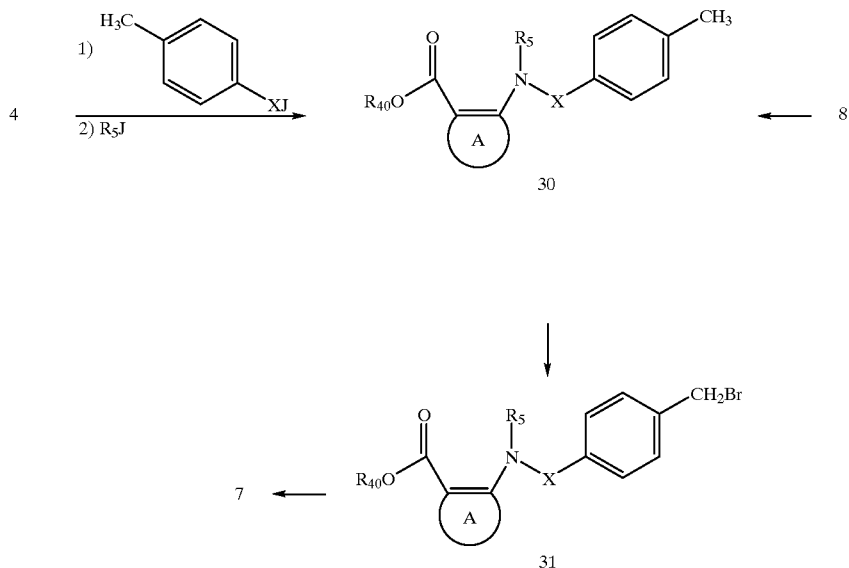

Compounds of the invention can also be prepared by modifying substituents on the acetylenic side chain at any stage after sulfonylation or phosphorylation of the starting amino acid derivatives 4 or 8. Functional groups such as halogen, hydroxy, amino, aldehyde, ester, ketone, etc. may be manipulated by standard methods to form the moieties defined by $R_1$–$R_8$ of compounds 1. It is recognized by those skilled in the art of organic synthesis that the successful use of these methods is dependent upon the compatibility of substituents on other parts of the molecule. Protecting groups and/or changes in the order of steps described herein may be required.

Some of the methods available for the derivatization of compounds of structure 32 (equivalent to compound 7 wherein $R_{12}$ is hydrogen) are shown in Scheme 9. Metallation of the terminal acetylene 32 followed by addition of an aldehyde or alkyl halide, sulfonate or triflate provides derivatives 33 and 34. Reaction of 32 with formaldehyde and an amine provides the Mannich addition product 35. Cyanogen bromide addition to 35 gives the propargylic compatibility of substituents on other parts of the molecule. Protecting groups and/or changes in the order of steps described herein may be required.

Scheme 9

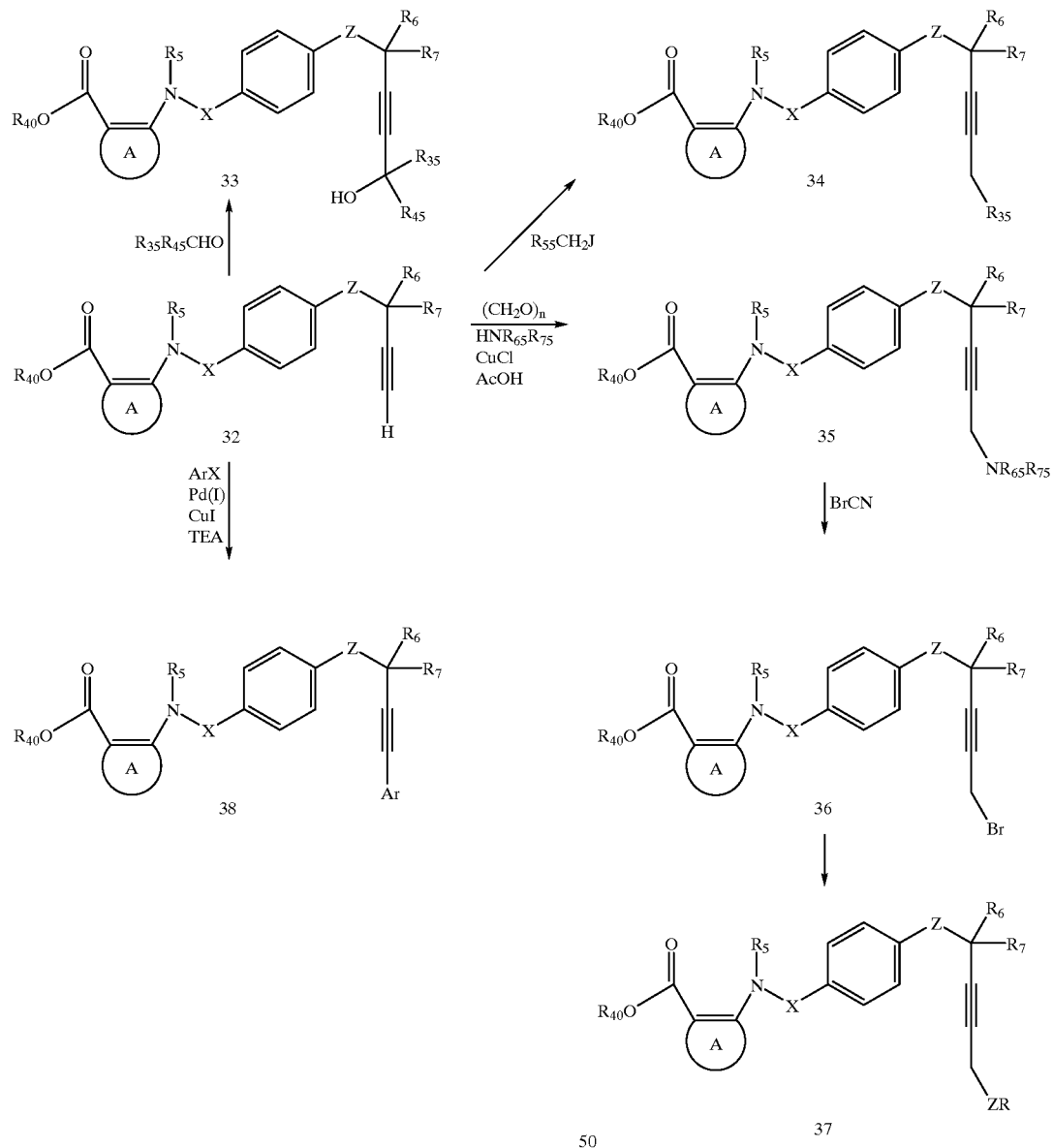

Shown in Scheme 10 is the synthesis of an example of the invention of the invention wherein A is pyridyl. In this specific example, shown for illustrative purposes only, the BOC-protected amino-pyridine 39 is synthesized from 3-amino-2,6-dimethoxypyridine via reaction with BOC anhydride. The ortho-amino ester, 40, is then constructed via metallation and subsequent carboxylation of 39. Removal of the BOC protecting group from ester 41 provides ortho amino-ester 42. Elaboration of 42 according to Schemes 1–9 then provides the compounds of the invention. Additional pyridyl-hydroxamates are available through the same route.

Scheme 10

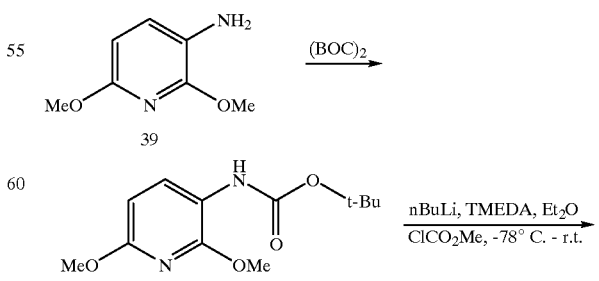

-continued

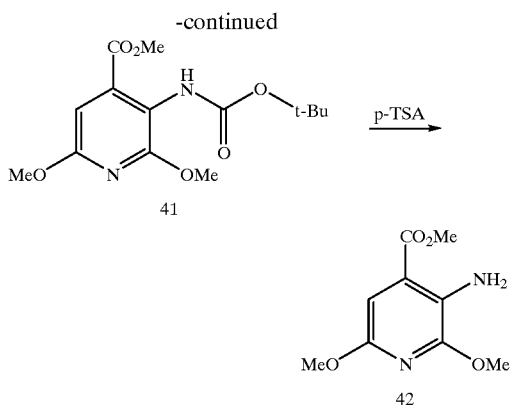

The following specific examples illustrate the preparation of representative compounds of this invention. The starting materials, intermediates, and reagents are either commercially available or can be readily prepared following standard literature procedures by one skilled in the art of organic synthesis.

EXAMPLE 1

3-(4-Methoxy-benzenesulfonylamino)-thiophene-2-carboxylic acid methyl ester

To a solution of 5.00 g (0.032 mol) of 3-amino-2-carbomethoxythiophene dissolved in 40 mL of chloroform was added 7.73 mL (0.032 mol) of pyridine followed by 6.57 g (0.032 mol) of p-methoxybenzenesulfonyl chloride. The reaction mixture was stirred at room temperature for 5 h and then washed with 3N HCl and water. The organics were then dried over $Na_2SO_4$, filtered and concentrated in vacuo. The resulting cream colored solid was washed with ether and dried in vacuo to provide 6.89 g (66%) of the desired sulfonamide. Electrospray Mass Spec 328.2 M+H).

EXAMPLE 2

4-(4-Methoxy-benzenesulfonylamino)-thiophene-3-carboxylic acid methyl ester

In the same manner as described in Example 1, 5.00 g (0.026 mol) of 3-amino-4-carbomethoxythiophene hydrochloride provided 3.50 g (41%) of the desired sulfonamide as a brown solid after trituration with ether. Electrospray Mass Spec 328.2 (M+H).

EXAMPLE 3

5-(4-Methoxy-benzenesulfonylamino)-1-methyl-1H-pyrazole-4-carboxylic acid ethyl ester In the same manner as described in Example 1, 2.00 g (0.012 mol) of 1-methyl-2-amino-3-carboethoxy-pyrazole provided 0.923 g (23%) of the desired sulfonamide as a white solid after recrystallization from ethyl acetate/Hexanes. Electrospray Mass Spec 340.2 (M+H).

EXAMPLE 4

3-(4-Methoxy-benzenesulfonylamino)-4-methyl-thiophene-2-carboxylic acid methyl ester In the same manner as described in Example 1, 4.14 g (0.024 mol) of 3-amino-4-methyl-2-carbomethoxy thiophene provided 4.89 g (47%) of the desired sulfonamide as a white solid after trituration with ether. EI Mass Spec 340.9 ($M^+$).

EXAMPLE 5

3-[Benzyl-(4-methoxy-benzenesulfonyl)-amino]-thiophene-2-carboxylic acid methyl ester To a solution of 2.0 g (6.116 mmol) of the product of Example 1 in 25 mL of DMF was added 0.257 g (6.422 mmol) of 60% sodium hydride. The resulting mixture was stirred for 30 min at room temperature and then 0.76 mL (6.422 mmol) of benzyl bromide was added. This reaction mixture was stirred overnight at room temperature, poured into water and then extracted with ether. The combined organics were washed with water and brine, dried over $MgSO_4$, filtered and concentrated in vacuo. The residue was chromatographed on silica gel eluting with ethyl actate/hexanes (1:3) to provide 1.62 g (65%) of the desired product as white crystals. CI Mass Spec: 418 (M+H).

EXAMPLE 6

4-[Benzyl-(4-methoxy-benzenesulfonyl)-amino]-thiophene-3-carboxylic acid methyl ester In the same manner as described in Example 5, 1.50 g (4.587 mmol) of the product of Example 2 provided 1.257 g (66%) of the desired product as a brown oil after chromatography on silica gel eluting with ethyl acetate/hexanes (1:10). CI Mass Spec: 418 (M+H).

EXAMPLE 7

5-[Benzyl-(4-methoxy-benzenesulfonyl)-amino]-1-methyl-1H-pyrazole-4-carboxylic acid ethyl ester In the same manner as described in Example 5, 0.843 g (2.484 mmol) of the product of Example 3 provided 0.924 g (87%) of the desired product as a white solid after trituration with ether. CI Mass Spec: 430 (M+H).

EXAMPLE 8

3-[Benzyl-(4-methoxy-benzenesulfonyl)-amino]-4-methyl-thiophene-2-carboxylic acid methyl ester In the same manner as described in Example 5, 2.00 g (4.64 mmol) of the product of Example 4 provided 1.648 g (68%) of the desired product as a white solid after trituration with ether. CI Mass Spec: 432 (M+H).

EXAMPLE 9

3-[Benzyl-(4-methoxy-benzenesulfonyl)-amino]-thiophene-2-carboxylic acid

To a mixture of 1.494 g (3.583 mmol) of the product of Example 5 dissolved in 15 mL of methanol and 15 mL of THF was added 15 mL of 1N NaOH solution. The reaction mixture was stirred at room temperature for 36 h and the organics were removed in vacuo. The resulting mixture was acidified with 10% HCl and extracted with ethyl acetate. The combined organics were washed with water and brine, dried over $MgSO_4$, filtered and concentrated in vacuo. The resulting residue was triturated with ether and filtered to provide 1.327 g (92%) of the desired carboxylic acid as a white solid. CI Mass Spec: 404 (M+H).

EXAMPLE 10

4-[Benzyl-(4-methoxy-benzenesulfonyl)-amino]-thiophene-3-carboxylic acid

In the same manner as described in Example 9, 1.157 g (2.775 mmol) of the product of Example 6 provided 0.94 g (84%) of the desired carboxylic acid as a tan solid after trituration with ether. Electrospray Mass Spec: 404 (M+H).

EXAMPLE 11

5-[Benzyl-(4-methoxy-benzenesulfonyl)-amino]-1-methyl-1H-pyrazole-4-carboxylic acid To a solution of 0.799 g (1.862 mmol) of the product of Example 7 in 20 mL of methanol/THF (1:1) was added 9.3 mL of 1N sodium hydroxide solution and the resulting mixture was heated to reflux for 18 h. The reaction was then cooled to room temperature and the organics were removed in vacuo. The resulting mixture was acidified with 10% HCl and extracted with ethyl acetate. The combined organics were washed with water and brine, dried over $MgSO_4$, filtered and concentrated in vacuo. The resulting residue was triturated with ether and filtered to provide 0.697 g (93%) of the desired carboxylic acid as a white solid. Electrospray Mass Spec: 402 (M+H).

EXAMPLE 12

3-[Benzyl-(4-methoxy-benzenesulfonyl)-amino]-4-methyl-thiophene-2-carboxylic acid In the same manner as described in Example 11, 1.366 g (2.622 mmol) of the product of Example 8 provided 1.16 g (87%) of the desired carboxylic acid as a white solid after trituration with ether. Electrospray Mass Spec: 416 (M−H)−.

EXAMPLE 13

5-Bromo-4-(4-methoxy-benzenesulfonylamino)-thiophene-3-carboxylic acid methyl ester To a solution of the product of Example 2 in 5.0 mL of acetic acid-chloroform (1:1) at room temperature was added 0.299 g (1.682 mmol) of N-bromosuccinimide. The reaction was stirred for 18 h and then diluted with ether, washed with water and saturated sodium bicarbonate solution, dried over $MgSO_4$, filtered and concentrated in vacuo. The tan solid residue was washed with ether-hexanes (1:1) to provide 0.504 g (81%) of the desired product as a tan solid. Electrospray Mass Spec: 406.1 (M+H)+

EXAMPLE 14

4-[Benzyl-(4-methoxy-benzenesulfonyl)-amino]-5-bromo-thiophene-3-carboxylic acid methyl ester In the same manner as described in Example 5, 0.424 g (1.044 mmol) of the product of Example 13 gave 0.400 g (77%) of the desired N-benzyl methyl ester as a white solid. Electrospray Mass Spec: 496.1 (M+H)+

EXAMPLE 15

4-[Benzyl-(4-methoxy-benzenesulfonyl)-amino]-5-bromo-thiophene-3-carboxylic acid In the same manner as described in Example 11, 0.356 g (0.718 mmol) of the product of Example 14 gave 0.290 g (84%) of the desired carboxylic acid as a white solid. Electrospray Mass Spec: 482.1 (M+H)+

EXAMPLE 16

4-[Benzyl-(4-methoxy-benzenesulfonyl)-amino]-5-ethynyl-thiophene-3-carboxylic acid methyl ester To a solution of 0.294 g (0.634 mmol) of the product of Example 14 in 2.5 mL of DMF and 2.5 mL of triethylamine was added 0.448 mL (3.168 mmol) of timethylsilylacetylene, 0.022 g (0.032 mmol) of bis(triphenylphosphine)-palladium(II)-dichloride and 3 mg of copper(I)iodide. The reaction mixture was then heated to 80° C. for 6 h and then cooled to room temperature and diluted with ether. The organics were washed with 5% HCl solution, water and brine, dried over $MgSO_4$, filtered and concentrated in vacuo. The residue was dissolved in 5 mL of THF, 1 mL of 1M tetrabutylammonium flouride-THF solution was added and the reaction was stirred at room temperature for 1 h, then diluted with ether, washed with 5% HCl solution, water and brine, dried over $MgSO_4$, filtered and concentrated in vacuo. The residue was chromatographed on silica eluting with ethyl acetate-hexanes (1:5) to provide 0.159 g (61%) of the desired product as a brown oil. Electrospray Mass Spec: 442.2 (M+H)+

EXAMPLE 17

4-[Benzyl-(4-methoxy-benzenesulfonyl)-amino]-5-ethynyl-thiophene-3-carboxylic acid In the same manner as described in Example 11, 0.136 g (0.333 mmol) of the product of Example 16 provided 0.075 g (57%) of the desired product as a tan solid after chromatography on silica eluting with ethyl acetate-hexanes (1:1). Electrospray Mass Spec: 428.1 (M+H)+

EXAMPLE 18

5-Bromo-4-[(4-methoxybenzenesulfonyl)-pyridin-3-ylmethylamino]thiophene-3-carboxylic acid methyl ester To a solution of 4.80 g (11.82 mmol) of the product of Example 13 dissolved in 5.0 mL of DMF was added 2.04 g (12.41 mmol) of 3-picolyl chloride hydrochloride and 4.89 g (35.46 mmol) of potassium carbonate. The reaction mixture was then stirred at room temperature for 18 h, diluted with water and extracted with ether. The organics were then extracted with 6N HCl solution and the aqueous acid layer was then basified with 6N NaOH solution and then extracted with ether. The resulting ether layer was dried over sodium sulfate, filtered and concentrated in vacuo to provide 4.16 g (71%) of the desired product as a tan solid. Electrospray Mass Spec: 498 (M+H).

EXAMPLE 19

5-Bromo-4-[(4-methoxy-benzenesulfonyl)-pyridin-3-ylmethyl-amino]-thiophene-3-carboxylic acid To a solution of 0.40 g (0.860 mmol) of the product of Example 18 in 9.0 mL of THF-MeOH (1:1) was added 0.072 g (1.72 mmol) of lithium hydroxide monohydrate. The reaction mix was heated to reflux for 18 h and then concentrated in vacuo. The residue was washed with THF and filtered. The filtrate was concentrated in vacuo to provide 0.388 g (100%) of the desired product as a white foam. Electrospray Mass Spec: 483 (M+H).

EXAMPLE 20 tert-Butyl N-(2,6-dimethoxy-3-pyridyl)carbamate

To a suspension of 3-amino-2,6-dimethoxypyridine (1.5 g, 7.87 mmol) was added di-tert-butyl dicarbonate (3.43 g, 15.7 mmol). The solution was heated at reflux for 36 hours, cooled to room temperature, and diluted with water. The aqueous solution was extracted 3 times with ethyl acetate, the organic extracts were combined, washed with brine, dried over MgSO$_4$, concentrated in vacuo. The residue was purified by column chromatography using hexane/ethyl acetate as eluant (gradient 100% to 4/1) to provide 2.00 g (100%) of tert-butyl N-(2,6-dimethoxy-3-pyridyl)carbamate a yellow oil. Electrospray Mass Spec: 254.9 (M+H)+

EXAMPLE 21 tert-Butyl N-(4-carbomethoxy-2,6-dimethoxy-3-pyridyl)carbamate

The product of Example 20 (1 g, 3.93 mmol) was dissolved in ether (35 mL) and TMEDA (1.7 mL, 1.18 mmol) and cooled to −78° C. n-Butyllithium (4.75 mL, 11.87 mmol) was added dropwise and the reaction was allowed to stir for 15 minutes at −78° C. before warming to −10° C. for 2.5 hours. The solution was cooled back to −78° C. and methyl chloroformate (0.6 mL, 7.8 mmol) dissolved in ether (4.5 mL) was added dropwise. The reaction was held at −78° C. for 10 minutes and then warmed to −10° C. and allowed to stir for 1.5 hours before quenching with ammonium chloride (sat). The reaction mixture was extracted 3× with ethyl acetate. The organics were combined, washed with brine, dried over MgSO$_4$, concentrated in vacuo. The residue was purified by column chromatography using hexane/ethyl acetate as eluant (gradient 9/1 to 4/1) to provide 0.423 g (34%) of tert-butyl N-(4-carbomethoxy-2,6-dimethoxy-3-pyridyl)carbamate as a white solid. Electrospray Mass Spec: 312.8 (M+H)+

EXAMPLE 22

Methyl 3-amino-2,6-dimethoxyisonicotinate p-Toluene sulfonic acid hydrate (0.282 g, 1.48 mmol) was dissolved in toluene (11 mL) and heated to reflux overnight with azeotropic removal of water (Dean-Stark trap). The next day, the reaction was cooled to room temperature and the product of Example 21, dissolved in toluene (4 mL), was added. The reaction was heated back to reflux for 0.5 hours. The reaction was cooled to room temperature and poured into sodium bicarbonate (sat) and extracted 3 times with ether. The organics were combined, washed with brine, dried over MgSO$_4$, concentrated in vacuo. The residue was purified by column chromatography using hexane/ethyl acetate as eluant (gradient 100% to 9/1) to provide 0.278 g (97%) of methyl 3-amino-2,6-dimethoxyisonicotinate as a yellow solid. Electrospray Mass Spec: 212.8 (M+H)+

EXAMPLE 23

Methyl 3-(4-methoxy-benzenesulfonylamino)-2,6-dimethoxy-isonicotinate

To a solution of the product of Example 22 (0.278 g, 1.31 mmol) in pyridine (2 mL) was added p-methoxybenzenesulfonyl chloride (0.28 g, 1.38 mmol). The reaction mixture was stirred at room temperature overnight and was then quenched with water. The mixture was extracted 3 times with ether. The organics were combined, washed with brine, dried over MgSO$_4$, concentrated in vacuo to provide 0.444 g (89%) of methyl 3-(4-methoxy-benzenesulfonylamino)-2,6-dimethoxy isonicotinate as a solid. Electrospray Mass Spec: 382.8 (M+H)+

EXAMPLE 24

Methyl 3-[Benzyl-(4-methoxy-benzenesulfonyl)-amino]-2,6-dimethoxy-isonicotinate

The product of Example 23 (0.444 g, 1.16 mmol) was dissolved in DMF (4 mL) and cooled to 0° C. Benzyl bromide (0.186 mL, 1.6 mmol) followed by sodium hydride (56 mg, 1.39 mmol, 60% dispersion in mineral oil) were added and the reaction was allowed to warm to room temperature. After 1 h, the reaction was diluted with water and extracted 4×ether. The organics were combined, washed with brine, dried over MgSO$_4$, concentrated in vacuo to provide 0.545 g (100%) of pure methyl 3-[Benzyl-(4-methoxy-benzenesulfonyl)-amino]-2,6-dimethoxy-isonicotinate as an oil. Electrospray Mass Spec: 472.9 (M+H)+

EXAMPLE 25

3-[Benzyl-(4-methoxy-benzenesulfonyl)-amino]-2,6-dimethoxy-isonicotinic acid

The product of Example 24 was hydrolyzed to the corresponding carboxylic acid using the procedure of Example 19 to provide 3-[Benzyl-(4-methoxy-benzenesulfonyl)-amino]-2,6-dimethoxy-isonicotinic acid. Electrospray Mass Spec: 459.0 (M+H)+

EXAMPLE 26

4-But-2-ynyloxy-benzenesulfonic acid sodium salt

To a solution of 52.35 g (0.225 mol) of 4-hydroxybenzenesulfonate sodium salt in 1L of isopropanol and 225 mL of a 1.0N solution of sodium hydroxide was added 59.96 g (0.45 mol) of 1-bromo-2-butyne. The resulting mixture was heated to 70° for 15 h and then the isopropanol was removed by evaporation in vacuo. The resulting white precipitate was collected by filtration, washed with isopropanol and ether and dried in vacuo to give 56.0 g (100%) of the butynyl ether as a white solid.

EXAMPLE 27

4-But-2-ynyloxy-benzenesulfonyl chloride

To a 0° solution of 43.8 mL (0.087 mol) of 2M oxalyl chloride/dichloro-methane solution in 29 mL of dichloromethane was dropwise added 6.77 mL (0.087 mol) of DMF followed by 7.24 g (0.029 mol) of the product of Example 26. The reaction mixture was stirred for 10 minutes at 0° then let warm to room temperature and stirred for 2 days. The reaction was then poured into ice and extracted with 150 mL of hexanes. The organics were washed with water and brine, dried over Na$_2$SO$_4$, filtered and concentrated in vacuo to provide 6.23 g (88%) of the sulfonyl chloride as a yellow solid; m.p. 63–65° C. EI Mass Spec: 243.9 (M$^+$).

EXAMPLE 28

But-2-ynyloxy-benzene

To a solution of 6.14 g (0.023 mol) of triphenylphosphine dissolved in 100 mL of benzene and 40 mL of THF was added 1.75 mL (0.023 mol) of 2-butyn-1-ol. After five minutes 2.00 (0.023 mol) phenol, dissolved in 10 mL of THF, was added to the reaction followed by 3.69 mL (0.023 mol) of diethyl azodicarboxylate. The resulting reaction mixture was stirred for 18 h at room temperature and then concentrated in vacuo. The residue was chromatographed on silica gel eluting with ethyl acetate/hexanes (1:10) to provide 2.18 g (70%) of the butynyl ether as a clear liquid. EI Mass Spec: 146.0 MH$^+$

EXAMPLE 29

4-But-2-ynyloxy-benzenesulfonyl chloride

To a solution of 0.146 g (1.0 mmol) of the product of Example 28 in 0.3 mL of dichloromethane in an acetone/ice bath under N$_2$ was dropwise added a solution of 0.073 mL (1.1 mmol) of chlorosulfonic acid in 0.3 mL of dichloromethane. After the addition was complete, the ice bath was removed and the reaction was stirred at room temperature for 2 h. To the reaction was then dropwise added 0.113 mL (1.3 mmol) of oxalyl chloride, followed by 0.015 mL DMF. The reaction was heated to reflux for 2 h and then diluted with hexane and poured into ice water. The organic layer was washed with brine, dried over sodium sulfate, and concentrated in vacuo to provide 0.130 mg (53%) of the desired product as a light brown solid.

EXAMPLE 30

Methyl 3-(4-but-2-ynyloxy-benzenesulfonylamino)-2,6-dimethoxy-isonicotinate

To a solution of the product of Example 22 (0.7 g, 3.3 mmol) in pyridine (6 mL) was added 4-but-2-ynyloxy-benzenesulfonyl chloride (0.8 g, 3.3 mmol). The reaction mixture was stirred at room temperature overnight and was then quenched with water. The mixture was extracted 3 times with ether. The organics were combined, washed with brine, dried over MgSO$_4$ and concentrated in vacuo. The residue was chromatographed on silica gel eluting with ethyl acetate/hexanes (gradient 1:1 to 7:3) to provide 1.15 g of the butynyloxybenzene sulfonamide as a solid. Electrospray Mass Spec: 421.1 (M+H)$^+$

EXAMPLE 31

Methyl 3-[Methyl-(4-but-2-ynyloxy-benzenesulfonyl)-amino]-2,6-dimethoxy-isonicotinate The product of Example 30 (0.48 g, 1.13 mmol) was dissolved in DMF (5 mL) and cooled to 0° C. Iodomethane (0.1 mL, 1.58 mmol) was added, followed by sodium hydride (0.054 g, 1.35 mmol, 60% dispersion in mineral oil) and the reaction was allowed to warm to room temperature. After 1 h, the reaction was diluted with water and extracted 4 times with ethyl acetate. The organics were combined, washed with brine, dried over MgSO$_4$, concentrated in vacuo to provide 0.23 g (48%) of the N-methyl sulfonamide as a white solid. Electrospray Mass Spec: 435.2 (M+H)$^+$

EXAMPLE 32

3-[Methyl -(4-but-2-ynyloxy-benzenesulfonyl)-amino]-2,6-dimethoxy-isonicotinic acid The product of Example 31 (0.214 g, 0.49 mmol) was hydrolyzed to the corresponding carboxylic acid using the procedure of Example 19 to provide 0.198 g (100%) of 3-[methyl-(4-but-2-ynyloxy-benzenesulfonyl)-amino]-2,6-dimethoxy-isonicotinic acid. Electrospray Mass Spec: 421.1 (M+H)$^+$

EXAMPLE 33

3-[Methyl-(4-but-2-ynyloxy-benzenesulfonyl)-amino]-N-hydroxy-2,6-dimethoxy-isonicotinamide To a solution of (0.15 g, 0.35 mmol) of the product from Example 32 in 2 mL of DMF was added 0.39 mL (0.77 mmol) of a 2M solution of oxalyl chloride in dichloromethane and the resulting reaction mixture was stirred at room temperature for 2 h.

In a separate flask, 0.77 mL (5.6 mmol) of triethylamine was added to a 0° C. mixture of 0.24 g (3.5 mmol) of hydroxylamine hydrochloride in 4 mL of THF and 1 mL of water. After this mixture had been stirred for 15 min at 0° C., the acid chloride solution was added to it in one portion and the resulting solution was allowed to warm to room temperature and stirred for another 3 h. The dichloromethane was was washed with brine, dried over MgSO$_4$, filtered and concentrated in vacuo. Trituration of the residue with ether provided 0.108 g (75%) of the hydroxamic acid as a white powder. Electrospray Mass Spec: 436.1 (M+H)$^+$

EXAMPLE 34

3-(4-But-2-ynyloxy-benzenesulfonyl)-amino-2,6-dimethoxy-isonicotinic acid

The product of Example 30 (0.400 g, 0.95 mmol) was hydrolyzed to the corresponding carboxylic acid using the procedure of Example 19 to provide 0.338 g (100%) of 3-(4-but-2-ynyloxy-benzenesulfonyl)-amino-2,6-dimethoxy-isonicotinic acid. Electrospray Mass Spec: 407.2 (M+H)$^+$

EXAMPLE 35

3-(4-But-2-ynyloxy-benzenesulfonylamino)-N-hydroxy-2,6-dimethoxy-isonicotinamide The product of Example 34 (86 mg, 0.21 mmol) was dissolved in DMF (2 mL). To this solution was added hydroxylamine hydrochloride (123 mg, 1.88 mmol), 1-hydroxybenzotriazole (68 mg, 0.5 mmol), triethylamine (0.3 mL, 2.1 mmol), and 1-(3-dimethylaminopropyl)-3-ethylcarbodiimide hydrochloride (113 mg, 0.59 mmol). The reaction mixture was stirred overnight and then filtered to remove the white precipitate. The filtrate was then diluted with dichloromethane, and washed with water, brine, dried over Na$_2$SO$_4$, filtered, concentrated in vacuo to provide an orange oil. The residue was chromatographed on silica gel eluting with ethyl acetate to provide 32 mg (36%) of the hydroxamic acid as a white solid. Electrospray Mass Spec: 422.2 (M+H)$^+$.

Pharmacology

The ability of the compounds of the invention, or their pharmaceutically acceptable salts, to inhibit matrix metalloproteinases or TACE and, consequently, demonstrate their effectiveness for treating diseases modulated by matrix metalloproteinases or TACE is shown by the following in vitro assays.

Test Procedures for Measuring MMP-1, MMP-9, and MMP-13 Inhibition

These standard pharmacological test procedures are based on the cleavage of a thiopeptide substrates such as Ac-Pro-Leu-Gly(2-mercapto-4-methyl-pentanoyl)-Leu-Gly-OEt by the matrix metalloproteinases MMP-1, MMP-13 (collagenases) or MMP-9 (gelatinase), which results in the release of a substrate product that reacts colorimetrically with DTNB (5,5'-dithiobis(2-nitro-benzoic acid)). The enzyme activity is measured by the rate of the color increase. The thiopeptide substrate is made up fresh as a 20 mM stock in 100% DMSO and the DTNB is dissolved in 100% DMSO as a 100 mM stock and stored in the dark at room temperature. Both the substrate and DTNB are diluted together to 1 mM with substrate buffer (50 mM HEPES pH 7.5, 5 mM CaCl$_2$) before use. The stock of enzyme is diluted with buffer (50 mM HEPES, pH 7.5, 5 mM CaCl$_2$, 0.02% Brij) to the desired final concentration. The buffer, enzyme, vehicle or inhibitor, and DTNB/substrate are added in this order to a 96 well plate (total reaction volume of 200 μl) and the increase in color is monitored spectrophotometrically for 5 minutes at 405 nm on a plate reader and the increase in color over time is plotted as a linear line.

Alternatively, a fluorescent peptide substrate is used. In this test procedure, the peptide substrate contains a fluorescent group and a quenching group. Upon cleavage of the substrate by an MMP, the fluorescence that is generated is quantitated on the fluorescence plate reader. The assay is run in HCBC assay buffer (50mM HEPES, pH 7.0, 5 mM $Ca^{+2}$, 0.02% Brij, 0.5% Cysteine), with human recombinant MMP-1, MMP-9, or MMP-13. The substrate is dissolved in methanol and stored frozen in 1 mM aliquots. For the assay, substrate and enzymes are diluted in HCBC buffer to the desired concentrations. Compounds are added to the 96 well plate containing enzyme and the reaction is started by the addition of substrate. The reaction is read (excitation 340 nm, emission 444 nm) for 10 min. and the increase in fluorescence over time is plotted as a linear line.

For either the thiopeptide or fluorescent peptide test procedures, the slope of the line is calculated and represents the reaction rate. The linearity of the reaction rate is confirmed ($r^2>0.85$). The mean (x±sem) of the control rate is calculated and compared for statistical significance ($p<0.05$) with drug-treated rates using Dunnett's multiple comparison test. Dose-response relationships can be generated using multiple doses of drug and $IC_{50}$ values with 95% CI are estimated using linear regression.

Test Procedure for Measuring TACE Inhibition

Using 96-well black microtiter plates, each well receives a solution composed of 10 μL TACE (final concentration 1 μg/mL), 70 μL Tris buffer, pH 7.4 containing 10% glycerol (final concentration 10 mM), and 10 μL of test compound solution in DMSO (final concentration 1 μM, DMSO concentration <1%) and incubated for 10 minutes at room temperature. The reaction is initiated by addition of a fluorescent peptidyl substrate (final concentration 100 μM) to each well and then shaking on a shaker for 5 sec.

The reaction is read (excitation 340 nm, emission 420 nm) for 10 min. and the increase in fluorescence over time is plotted as a linear line. The slope of the line is calculated and represents the reaction rate.

The linearity of the reaction rate is confirmed ($r^2>0.85$). The mean (x±sem) of the control rate is calculated and compared for statistical significance ($p<0.05$) with drug-treated rates using Dunnett's multiple comparison test. Dose-response relationships can be generate using multiple doses of drug and $IC_{50}$ values with 95% CI are estimated using linear regression.

Human Monocytic THP-1 Cell Differentiation Assay For Soluble Proteins (THP Soluble Protein Assay)

Mitogenic stimulation of THP-1 cells cause differentiation into macrophage like cells with concomitant secretion of tumor necrosis factor (TNF-α) and TNF receptor (TNF-R p75/80 and TNF-R p55/60) and Interleukin-8 (IL-8), among other proteins. In addition, non-stimulated THP-1 cells shed both the p75/80 and the p55/60 receptors over time. The release of membrane bound TNF-α and possibly TNF-R p75/80 and TNF-R p55/60, but not IL-8, is mediated by an enzyme called TNF-α converting enzyme or TACE. This assay can be used to demonstrate either an inhibitory or a stimulatory compound effect on this TACE enzyme and any cytotoxic consequence of such a compound.

THP-1 cells (from ATCC) are a human monocytic cell line which were obtained from the peripheral blood of a one year old male with acute monocytic leukemia. They can be grown in culture and differentiated into macrophage like cells by stimulation with mitogens.

For the assay, THP-1 cells are seeded from an ATCC stock which was previously grown and frozen back at 5×106/ml/vial. One vial is seeded into a T25-flask with 16 mls of RPMI-1640 with glutamax (Gibco) media containing 10% fetal bovine serum, 100 units/ml penicillin, 100 μg/ml streptomycin, and $5 \times 10^{-5}$ M 2-mercapto-ethanol (THP-1 media). Each vial of cells are cultured for about two weeks prior to being used for an assay and then are used for only 4 to 6 weeks to screen compounds. Cells are subcultured on Mondays and Thursdays to a concentration of 1×105/ml.

To perform an assay, the THP-1 cells are co-incubated in a 24 well plate with 50 m/well of a 24 mg/ml stock of Lipopolysachride (LPS) (Calbiochem Lot# B13189) at 37° C. in 5% $CO_2$ at a concentration of $1.091 \times 10^6$ cells/ml (1.1 ml/well) for a total of 24 hours. At the same time, 50 ml/well of drug, vehicle or THP-1 media is plated in appropriate wells to give a final volume of 1.2 ml/well. Standard and test compounds are dissolved in DMSO at a concentration of 36 mM and diluted from here to the appropriate concentrations in THP-1 media and added to the wells at the beginning of the incubation period to give final concentrations of 100 mM, 30 mM, 10 mM, 3 mM, 1 mM, 300 nM, and 100 nM. Cell exposure to DMSO was limited to 0.1% final concentration. Positive control wells were included in the experiment which had mitogen added but no drug. Vehicle control wells were included as well, which were identical to the positive control wells, except that DMSO was added to give a final concentration of 0.083%. Negative control wells were included in the experiment which had vehicle but no mitogen or drug added to the cells. Compounds can be evaluated for their effect on basal (non-stimulated) shedding of the receptors by replacing the LPS with 50 ml/well of THP-1 media. Plates are placed into an incubator set at 5% CO2 and at 37° C. After 4 hours of incubation, 300 ml/well of tissue culture supernatant (TCS) is removed for use in an TNF-α ELISA. Following 24 hours of incubation, 700 ml/well of TCS is removed and used for analysis in TNF-R p75/80, TNF-R p55/60 and IL-8 ELISAs.

In addition, at the 24 hours timepoint, and the cells for each treatment group are collected by resuspension in 500 μl/well of THP-1 media and transferred into a FACS tube. Two ml/tube of a 0.5 mg/ml stock of propidium iodide (PI) (Boerhinger Mannheim cat. # 1348639) is added. The samples are run on a Becton Dickinson FaxCaliber FLOW cytometry machine and the amount of dye taken up by each cell is measured in the high red wavelength (FL3). Only cells with compromised membranes (dead or dying) can take up PI. The percent of live cells is calculated by the number of cells not stained with PI, divided by the total number of cells in the sample. The viability values calculated for the drug treated groups were compared to the viability value calculated for the vehicle treated mitogen stimulated group ("vehicle positive control") to determine the "percent change from control". This "percent change from control" value is an indicator of drug toxicity.

The quantity of soluble TNF-α, TNF-R p75/80 and TNF-R p55/60 and IL-8 in the TCS of the THP-1 cell cultures are obtained with commercially available ELISAs from R&D Systems, by extrapolation from a standard curve generated with kit standards. The number of cells that either take up or exclude PI are measured by the FLOW cytometry machine and visualized by histograms using commercially available Cytologic software for each treatment group including all controls.

Biological variability in the magnitude of the response of THP-1 cell cultures requires that experiments be compared on the basis of percent change from "vehicle positive control" for each drug concentration Percent change in each soluble protein evaluated from the "vehicle positive control" was calculated for each compound concentration with the following formula:

$$\% \text{ Change} = \frac{\text{pg/ml (compound)} - \text{pg/ml (veh pos control)}}{\text{pg/ml (veh pos control)} - \text{pg/ml (veh neg contol)}} \times 100$$

For the soluble protein (TNF-α, p75/80, p55/60, IL-8) studies under stimulated conditions, the mean pg/ml of duplicate wells were determined and the results expressed as percent change from "vehicle positive control". For the soluble protein (p75/80 and p55/60 receptors) studies under non-stimulated conditions, the mean pg/ml of duplicate wells were determined and the results expressed as percent change from "vehicle positive control" utilizing the following formula:

$$\% \text{ Change} = \frac{\text{pg/ml (compound neg control)} - \text{pg/ml (veh neg control)}}{\text{pg/ml (veh neg control)}} \times 100$$

$IC_{50}$ values for each compound are calculated by non-linear regression analysis using customized software utilizing the JUMP statistical package.

For the cell viability studies, the viabilities (PI exclusion) of pooled duplicate wells were determined and the results expressed as % change from "vehicle positive control". The viability values calculated for the compound treated groups were compared to the viability value calculated for the "vehicle positive control" to determine "percent change from control" as below. This value "percent change from control" is an indicator of drug toxicity.

$$\% \text{ Change} = \frac{\% \text{ live cells (compound)}}{\% \text{ live cells (veh pos control)}} - 1 \times 100$$

References

Bjornberg, F., Lantz, M., Olsson, I., and Gullberg, U. Mechanisms involved in the processing of the p55 and the p75 tumor necrosis factor (TNF) receptors to soluble receptor forms. Lymphokine Cytokine Res. 13:203–211, 1994.

Gatanaga, T., Hwang, C., Gatanaga, M., Cappuccini, F., Yamamoto, R., and Granger, G. The regulation of TNF mRNA synthesis, membrane expression, and release by PMA- and LPS-stimulated human monocytic THP-1 cells in vitro. Cellular Immun. 138:1–10, 1991.

Tsuchiya, S., Yamabe, M., Yamagughi, Y., Kobayashi, Y., Konno, T., and Tada, K. Establishment and characterization of a human acute monocytic leukemia cell line (THP-1). Int. J. Cancer. 26:1711–176, 1980.

Results of the above in vitro matrix metalloproteinase inhibition, TACE inhibition, and THP standard pharmacological test procedures are given in Table 1.

TABLE 1

| Example # | R | MMP-1[a] | MMP-9[a] | MMP-13[a] | TACE[a] | THP[b] |
|---|---|---|---|---|---|---|
| 33 | Me | ~10,000 | 607 | 478 | 11 | 31 |
| 35 | H | — | — | — | 44 | — |

[a]$IC_{50}$ (nM)
[b]% Inhibition @ 3 μM

Based on the standard pharmacological test procedures described above, the compounds of this invention are useful in the treatment of disorders such as arthritis, tumor metastasis, tissue ulceration, abnormal wound healing, periodontal disease, graft rejection, insulin resistance, bone disease and HIV infection.

The compounds of this invention are also useful in treating or inhibiting pathological changes mediated by matrix metalloproteinases such as atherosclerosis, atherosclerotic plaque formation, reduction of coronary thrombosis from atherosclerotic plaque rupture, restenosis, MMP-mediated osteopenias, inflammatory diseases of the central nervous system, skin aging, angiogenesis, tumor metastasis, tumor growth, osteoarthritis, rheumatoid arthritis, septic arthritis, corneal ulceration, proteinuria, aneurysmal aortic disease, degenerative cartilage loss following traumatic joint injury, demyelinating diseases of the nervous system, cirrhosis of the liver, glomerular disease of the kidney, premature rupture of fetal membranes, inflammatory bowel disease, age related macular degeneration, diabetic retinopathy, proliferative vitreoretinopathy, retinopathy of prematurity, ocular inflammation, keratoconus, Sjogren's syndrome, myopia, ocular tumors, ocular angiogenesis/neovascularization and corneal graft rejection.

Compounds of this invention may be administered neat or with a pharmaceutical carrier to a patient in need thereof. The pharmaceutical carrier may be solid or liquid.

Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such a solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g., cellulose derivatives, preferable sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

The compounds of this invention may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels, and occlusive devices. The creams and ointments may be viscous liquid or semi-solid emulsions of either the oil in water or water in oil type. Pastes comprised of absorptive powders dispersed in petroleum or hydrophilic petroleum containing the active ingredient may also be suitable. A variety of occlusive devices may be used to release the active ingredient into the blood stream such as a semipermeable membrane covering a reservoir containing the active ingredient with or without a carrier, or a matrix containing the active ingredient. Other occlusive devices are known in the literature.

The dosage to be used in the treatment of a specific patient suffering a MMP or TACE dependent condition must be subjectively determined by the attending physician. The variables involved include the severity of the dysfunction, and the size, age, and response pattern of the patient. Treatment will generally be initiated with small dosages less than the optimum dose of the compound. Thereafter the dosage is increased until the optimum effect under the circumstances is reached. Precise dosages for oral, parenteral, nasal, or intrabronchial administration will be determined by the administering physician based on experience with the individual subject treated and standard medical principles.

Preferably the pharmaceutical composition is in unit dosage form, e.g., as tablets or capsules. In such form, the composition is sub-divided in unit dose containing appropriate quantities of the active ingredient; the unit dosage form can be packaged compositions, for example packed powders, vials, ampoules, prefilled syringes or sachets containing liquids. The unit dosage form can be, for example, a capsule or tablet itself, or it can be the appropriate number of any such compositions in package form.

What is claimed:

1. A compound of the formula:

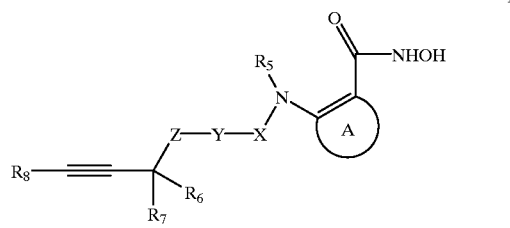

where the C(=O)NHOH moiety and the —NR$^5$— moiety are bonded to adjacent carbons of group A; wherein A is 5–6 membered heteroaryl having 1 to 3 heteroatoms selected from N, NR9, S and O;

X is SO$_2$ or —P(O)R$_{10}$;

Y is aryl or 5–10 membered mono- or bi-cyclic heteroaryl having from 1 to three heteroatoms selected from N, NR9, S and O, with the proviso that X and Z may not be bonded to adjacent atoms of Y;

Z is O, NH, CH$_2$ or S;

R$_5$ is hydrogen or alkyl of 1–6 carbon atoms;

R$_6$ and R$_7$ are each, independently, hydrogen, alkyl of 1–6 carbon atoms, —CN, —CCH;

R$_8$ is hydrogen, alkyl of 1–6 carbon atoms, alkenyl of 2–6 carbon atoms, alkynyl of 2–6 carbon atoms, cycloalkyl of 3–6 carbon atoms, aryl, 5 to 10 membered heteroaryl having 1 to 3 heteroatoms selected from N, NR9, S and O, or 5 to 9 membered heterocycloalkyl having 1 or 2 heteroatoms selected from N, NR9, S and O;

R$_9$ is hydrogen, aryl, alkyl of 1–6 carbon atoms or cycloalkyl of 3–6 carbon atoms;

and R$_{10}$ is alkyl of 1–6 carbon atoms, cycloalkyl of 3–6 carbon atoms, aryl, or heteroaryl; or a pharmaceutically acceptable salt thereof.

2. A compound of structure B according to claim 1 wherein the ring atom of A adjacent the —NR$^5$— group is carbon and has a substituent other than hydrogen.

3. A compound according to claim 2 wherein Y is a phenyl ring substituted at the 1- and 4-positions by X and Z, respectively.

4. A compound according to claim 3 wherein X is SO$_2$.

5. A compound according to claim 3 wherein X is SO$_2$ and Z is oxygen.

6. A compound according to claim 3 wherein X is SO$_2$, Z is oxygen, and R$_6$ and R$_7$ are hydrogen.

7. A compound according to claim 3 wherein X is SO$_2$, Z is oxygen, R$_6$ and R$_7$ are hydrogen, and R$_8$ is —CH$_2$OH or methyl.

8. A compound according to claim 1 which is (3-[methyl-(4-but-2-ynyloxy-benzenesulfonyl-amino]-N-hydroxy-2,6-dimethoxy-isonicotinamide.

9. A compound according to claim 1 which is 3-(4-But-2-ynyloxy-benzenesulfonylamino)-N-hydroxy-2,6-dimethoxy-isonicotinamide.

10. A method of inhibiting pathological changes mediated by TNF-α converting enzyme (TACE) in a mammal in need thereof which comprises administering to said mammal a therapeutically effective amount of a compound having the formula

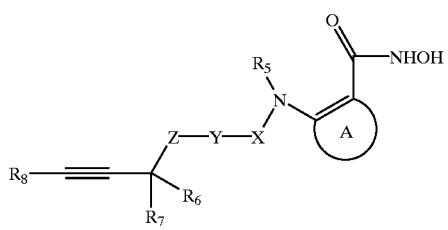

where the C(=O)NHOH moiety and the —NR⁵— moiety are bonded to adjacent carbons of group A; wherein A is 5–6 membered heteroaryl having 1 to 3 heteroatoms selected from N, NR9, S and O;

X is $SO_2$ or —P(O)$R_{10}$;

Y is aryl or 5–10 membered mono- or bi-cyclic heteroaryl having from 1 to three heteroatoms selected from N, NR9, S and O, with the proviso that X and Z may not be bonded to adjacent atoms of Y;

Z is O, NH, $CH_2$ or S;

$R_5$ is hydrogen or alkyl of 1–6 carbon atoms;

$R_6$ and $R_7$ are each, independently, hydrogen, alkyl of 1–6 carbon atoms, —CN, —CCH;

$R_8$ is hydrogen, alkyl of 1–6 carbon atoms, alkenyl of 2–6 carbon atoms, alkynyl of 2–6 carbon atoms, cycloalkyl of 3–6 carbon atoms, aryl, 5 to 10 membered heteroaryl having 1 to 3 heteroatoms selected from N, NR9, S and O, or 5 to 9 membered heterocycloalkyl having 1 or 2 heteroatoms selected from N, NR9, S and O;

$R_9$ is hydrogen, aryl, alkyl of 1–6 carbon atoms or cycloalkyl of 3–6 carbon atoms;

and $R_{10}$ is alkyl of 1–6 carbon atoms, cycloalkyl of 3–6 carbon atoms, aryl, or hetcroaryl; or a pharmaceutically acceptable salt thereof.

11. The method according to claim 10 wherein the condition treated is rheumatoid arthritis, graft rejection, cachexia, inflammation, fever, insulin resistance, septic shock, congestive heart failure, inflammatory disease of the central nervous system, inflammatory bowel disease or HIV infection.

12. A pharmaceutical composition comprising a compound having the formula

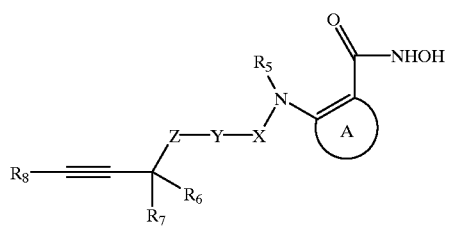

where the C(=O)NHOH moiety and the —NR⁵— moiety are bonded to adjacent carbons of group A; wherein A is 5–6 membered heteroaryl having 1 to 3 heteroatoms selected from N, NR9, S and O;

X is $SO_2$ or —P(O)$R_{10}$;

Y is aryl or 5–10 membered mono- or bi-cyclic heteroaryl having from 1 to three heteroatoms selected from N, NR9, S and O, with the proviso that X and Z may not be bonded to adjacent atoms of Y;

Z is O, NH, $CH_2$ or S;

$R_5$ is hydrogen or alkyl of 1–6 carbon atoms;

$R_6$ and $R_7$ are each, independently, hydrogen, alkyl of 1–6 carbon atoms, —CN, —CCH;

$R_8$ is hydrogen, alkyl of 1–6 carbon atoms, alkenyl of 2–6 carbon atoms, alkynyl of 2–6 carbon atoms, cycloalkyl of 3–6 carbon atoms, aryl, 5 to 10 membered heteroaryl having 1 to 3 heteroatoms selected from N, NR9, S and O, or 5 to 9 membered heterocycloalkyl having 1 or 2 heteroatoms selected from N, NR9, S and O;

$R_9$ is hydrogen, aryl, alkyl of 1–6 carbon atoms or cycloalkyl of 3–6 carbon atoms;

and $R_{10}$ is alkyl of 1–6 carbon atoms, cycloalkyl of 3–6 carbon atoms, aryl, or heteroaryl; or a pharmaceutically acceptable salt thereof; and a pharmaceutically acceptable carrier.

* * * * *